United States Patent [19]
Beckmann et al.

[11] Patent Number: 5,573,924
[45] Date of Patent: Nov. 12, 1996

[54] CD27 LIGAND

[75] Inventors: M. Patricia Beckmann, Poulsbo; Raymond G. Goodwin; Judith G. Giri, both of Seattle; Richard J. Armitage, Bainbridge Island, all of Wash.

[73] Assignee: Immunex Corporation, Seattle, Wash.

[21] Appl. No.: 106,507

[22] Filed: Aug. 13, 1993

Related U.S. Application Data

[63] Continuation-in-part of Ser. No. 941,648, Sep. 8, 1992, abandoned.

[51] Int. Cl.$^6$ .......................... C12N 15/19; C07K 14/52
[52] U.S. Cl. ................. 435/69.5; 435/240.2; 435/252; 435/3; 435/320.1; 530/351; 536/23.5; 930/140
[58] Field of Search ..................... 530/350, 351, 530/403, 399; 536/23.5; 435/69.3, 69.5 X, 240.1, 240.2, 252.3, 320.1; 930/140

[56] References Cited

U.S. PATENT DOCUMENTS 4,816,567   3/1989   Cabilly et al. ........................... 530/387

OTHER PUBLICATIONS

M R. Bowman et al. J. Immunol. 152(4):1756–1761 Feb. 15, 1994.
K. Paloczi et al. Haematologia 24(2):83–90 1991.
K. Paloczi et al. Leukemia & Lymphoma 3(1):31–36 1990.
S. Pileri et al. Histopathology 16(4):383–391 Apr. 1990.
A. Aruffo et al PNAS 84:8573–77 Dec. 1987.
Bigler et al., "S152 (CD27): A Modulating Disulfide–Linked T Cell Activation Antigen", *J. Immunol.* 141:21–28; 1988.
van Lier et al., "Tissue Distribution and Biochemical and Functional Properties of Tp55 (CD27), a Novel T Cell Differentiation Antigen", *J. Immunol.* 139:1589–1596; 1987.
Maurer et al., "CD27 Expression by a Distinct Subpopulation of Human B Lymphocytes", *Eur. J. Immunol.*, 20:2679–2684, 1990.
de Jong et al., "Regulation of Expression of CD27, a T Cell–Specific Member of a Novel Family of Membrane Receptors", *J. Immunol.*, 146:2488–2494, 1991.
van Lier et al., "Anti–CD27 Monoclonal Antibodies Identify Two Functionally Distinct Subpopulations within the CD4$^+$ T Cell Subset", *Eur. J. Immunol.*, 18:811–816, 1988.
Maurer et al.,"IgM and IgG but Not Cytokine Secretion is Restricted to the CD27$^+$ B Lymphocyte Subset", *J. Immunol.* 148:3700 –3705, 1992.
Camerini et al., "The T Cell Activation Antigen CD27 is a Member of the Nerve Growth Factor/Tumor Necrosis Factor Receptor Gene Family", *J. Immunol.*, 147:3165–3169, 1991.
Sugita et al., "The 1A4 Molecule (CD27) is Involved in T Cell Activation", *J. Immunol.* 147:1477–1483; 1991.
Gearing et al., "Expression cloning of a receptor for human granulocyte–macrophage colony–stimulating factor", *EMBO J.* 8:3667–3676; 1989.
Armitage et al., "Molecular and biological characterization of a murine ligand for CD40", *Nature* 357:80–82; 1992.
Riordan and Martin, "Oligonucleotide–based therapeutics", *Nature* 350:442, 1991.
Sims et al., "cDNA Expression Cloning of the IL–1 Receptor, a Member of the Immunoglobulin Superfamily", *Science* 241:585–589; 1988.
Yamasaki et al., "Cloning and Expression of the Human Interleukin–6 (BSF–2/IFNβ 2) Receptor", *Science* 241:825–828; 1988.
Hintzen et al., "A Soluble Form of the Human T Cell Differentiation Antigen CD27 is Released After Triggering of the TCR/CD3 Complex," *Journ. of Immun.* 147(1):29–35, 1991.

*Primary Examiner*—Garnette D. Draper
*Assistant Examiner*—Lorraine M. Spector
*Attorney, Agent, or Firm*—Seed and Berry LLP

[57] ABSTRACT

CD27 ligand (CD27L) polypeptide and DNA sequences, vectors and transformed host cells useful in providing CD27L polypeptides. The CD27L polypeptide binds to the CD27 receptor.

12 Claims, 6 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 926 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( B ) STRAIN: B CELL
        ( C ) INDIVIDUAL ISOLATE: EBV- TRANSFORMED ( v i i ) IMMEDIATE SOURCE:
        ( B ) CLONE: CD27L60

( i x ) FEATURE:
        ( A ) NAME/KEY: mat_peptide
        ( B ) LOCATION: 151..729

( i x ) FEATURE:
        ( A ) NAME/KEY: CDS
        ( B ) LOCATION: 151..732

( x i ) SEQUENCE DESCRIPTION: SEQ ID NO:1:

```
CCAGAGAGGG  GCAGGCTTGT  CCCCTGACAG  GTTGAAGCAA  GTAGACGCCC  AGGAGCCCCG      60

GGAGGGGGCT  GCAGTTTCCT  TCCTTCCTTC  TCGGCAGCGC  TCCGCGCCCC  CATCGCCCCT     120

CCTGCGCTAG  CGGAGGTGAT  CGCCGCGGCG  ATG  CCG  GAG  GAG  GGT  TCG  GGC  TGC     174
                                    Met  Pro  Glu  Glu  Gly  Ser  Gly  Cys
                                     1                    5

TCG  GTG  CGG  CGC  AGG  CCC  TAT  GGG  TGC  GTC  CTG  CGG  GCT  GCT  TTG  GTC   222
Ser  Val  Arg  Arg  Arg  Pro  Tyr  Gly  Cys  Val  Leu  Arg  Ala  Ala  Leu  Val
     10                  15                       20

CCA  TTG  GTC  GCG  GGC  TTG  GTG  ATC  TGC  CTC  GTG  GTG  TGC  ATC  CAG  CGC   270
Pro  Leu  Val  Ala  Gly  Leu  Val  Ile  Cys  Leu  Val  Val  Cys  Ile  Gln  Arg
 25                       30                       35                       40

TTC  GCA  CAG  GCT  CAG  CAG  CAG  CTG  CCG  CTC  GAG  TCA  CTT  GGG  TGG  GAC   318
Phe  Ala  Gln  Ala  Gln  Gln  Gln  Leu  Pro  Leu  Glu  Ser  Leu  Gly  Trp  Asp
                    45                       50                       55

GTA  GCT  GAG  CTG  CAG  CTG  AAT  CAC  ACA  GGA  CCT  CAG  CAG  GAC  CCC  AGG   366
Val  Ala  Glu  Leu  Gln  Leu  Asn  His  Thr  Gly  Pro  Gln  Gln  Asp  Pro  Arg
          60                       65                       70

CTA  TAC  TGG  CAG  GGG  GGC  CCA  GCA  CTG  GGC  CGC  TCC  TTC  CTG  CAT  GGA   414
Leu  Tyr  Trp  Gln  Gly  Gly  Pro  Ala  Leu  Gly  Arg  Ser  Phe  Leu  His  Gly
               75                       80                       85

CCA  GAG  CTG  GAC  AAG  GGG  CAG  CTA  CGT  ATC  CAT  CGT  GAT  GGC  ATC  TAC   462
Pro  Glu  Leu  Asp  Lys  Gly  Gln  Leu  Arg  Ile  His  Arg  Asp  Gly  Ile  Tyr
     90                       95                      100

ATG  GTA  CAC  ATC  CAG  GTG  ACG  CTG  GCC  ATC  TGC  TCC  TCC  ACG  ACG  GCC   510
Met  Val  His  Ile  Gln  Val  Thr  Leu  Ala  Ile  Cys  Ser  Ser  Thr  Thr  Ala
105                      110                      115                      120

TCC  AGG  CAC  CAC  CCC  ACC  ACC  CTG  GCC  GTG  GGA  ATC  TGC  TCT  CCC  GCC   558
Ser  Arg  His  His  Pro  Thr  Thr  Leu  Ala  Val  Gly  Ile  Cys  Ser  Pro  Ala
                    125                      130                      135

TCC  CGT  AGC  ATC  AGC  CTG  CTG  CGT  CTC  AGC  TTC  CAC  CAA  GGT  TGT  ACC   606
Ser  Arg  Ser  Ile  Ser  Leu  Leu  Arg  Leu  Ser  Phe  His  Gln  Gly  Cys  Thr
          140                      145                      150

ATT  GTC  TCC  CAG  CGC  CTG  ACG  CCC  CTG  GCC  CGA  GGG  GAC  ACA  CTC  TGC   654
Ile  Val  Ser  Gln  Arg  Leu  Thr  Pro  Leu  Ala  Arg  Gly  Asp  Thr  Leu  Cys
               155                      160                      165

ACC  AAC  CTC  ACT  GGG  ACA  CTT  TTG  CCT  TCC  CGA  AAC  ACT  GAT  GAG  ACC   702
Thr  Asn  Leu  Thr  Gly  Thr  Leu  Leu  Pro  Ser  Arg  Asn  Thr  Asp  Glu  Thr
170                      175                      180

TTC  TTT  GGA  GTG  CAG  TGG  GTG  CGC  CCC  TGACCACTGC  TGCTGATTAG                749
Phe  Phe  Gly  Val  Gln  Trp  Val  Arg  Pro
185                      190

GGTTTTTTAA  ATTTTATTTT  ATTTTATTTA  AGTTCAAGAG  AAAAAGTGTA  CACACAGGGG     809

CCACCCGGGG  TTGGGGTGGG  AGTGTGGTGG  GGGGTAGTTT  GTGGCAGGAC  AAGAGAAGGC     869

ATTGAGCTTT  TTCTTTCATT  TTCCTATTAA  AAAATACAAA  AATCAAAACA  AAAAAAA       926
```

( 2 ) INFORMATION FOR SEQ ID NO:2:

( i ) SEQUENCE CHARACTERISTICS:
        ( A ) LENGTH: 193 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Glu  Glu  Gly  Ser  Gly  Cys  Ser  Val  Arg  Arg  Arg  Pro  Tyr  Gly
 1                    5                       10                      15
```

-continued

```
Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                      70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Val Ser Gln Arg Leu Thr Pro
145                     150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: oligonucleotide ( x i ) SEQUENCE DESCRIPTION: SEQ ID NO:3:

ATAGCGGCCG CCTGGGCAGG GACCATG        27

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: oligonucleotide ( x i ) SEQUENCE DESCRIPTION: SEQ ID NO:4:

GTGACCGGTG GGGTTTCTAG GGACCTCGGG TCTAGAGCG    39

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: oligonucleotide ( x i ) SEQUENCE DESCRIPTION: SEQ ID NO:5:

GATCTTGGAA CGAGACGACC TGCT    24

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: oligonucleotide ( x i ) SEQUENCE DESCRIPTION: SEQ ID NO:6:

AACCTTGCTC TGCTGGACGA    20

( 2 ) INFORMATION FOR SEQ ID NO:7:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: oligonucleotide ( x i ) SEQUENCE DESCRIPTION: SEQ ID NO:7:

CTGTTGGGCT CGCGGTTGAG GACAAACTCT TCGCGGTCTT TCCAGT    46

( 2 ) INFORMATION FOR SEQ ID NO:8:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
    ( B ) CLONE: oligonucleotide ( x i ) SEQUENCE DESCRIPTION: SEQ ID NO:8:

GACAACCCGA GCGCCAACTC CTGTTTGAGA AGCGCCAGAA AGGTCA 46

( 2 ) INFORMATION FOR SEQ ID NO:9:

( i ) SEQUENCE CHARACTERISTICS:
        ( A ) LENGTH: 689 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: CD27 ligand trimer (CD27L-3)

( i x ) FEATURE:
        ( A ) NAME/KEY: CDS
        ( B ) LOCATION: 39..689

( i x ) FEATURE:
        ( A ) NAME/KEY: sig_peptide
        ( B ) LOCATION: 39..110

( i x ) FEATURE:
        ( A ) NAME/KEY: mat_peptide
        ( B ) LOCATION: 111..686

( x i ) SEQUENCE DESCRIPTION: SEQ ID NO:9:

```
GGAAAACTCT CGAGGTACCT ATCCCGGGGA TCCCCACC ATG TTC CAT GTC TCT       53
                                         Met Phe His Val Ser
                                         -24            -20

TTT AGA TAT ATC TTT GGA ATT CCT CCA CTG ATC CTT GTT CTG CTG CCT   101
Phe Arg Tyr Ile Phe Gly Ile Pro Pro Leu Ile Leu Val Leu Leu Pro
            -15             -10                      -5

GTC ACT AGT TCT GAC CGT ATG AAA CAG ATA GAG GAT AAG ATC GAA GAG   149
Val Thr Ser Ser Asp Arg Met Lys Gln Ile Glu Asp Lys Ile Glu Glu
             1               5              10

ATC CTA AGT AAG ATT TAT CAT ATA GAG AAT GAA ATC GCC CGT ATC AAA   197
Ile Leu Ser Lys Ile Tyr His Ile Glu Asn Glu Ile Ala Arg Ile Lys
         15              20              25

AAG CTG ATT GGC GAG CGG ACT AGT CAG CGC TTC GCA CAG GCT CAG CAG   245
Lys Leu Ile Gly Glu Arg Thr Ser Gln Arg Phe Ala Gln Ala Gln Gln
 30              35              40                      45

CAG CTG CCG CTC GAG TCA CTT GGG TGG GAC GTA GCT GAG CTG CAG CTG   293
Gln Leu Pro Leu Glu Ser Leu Gly Trp Asp Val Ala Glu Leu Gln Leu
             50              55                       60

AAT CAC ACA GGA CCT CAG CAG GAC CCC AGG CTA TAC TGG CAG GGG GGC   341
Asn His Thr Gly Pro Gln Gln Asp Pro Arg Leu Tyr Trp Gln Gly Gly
             65              70                       75

CCA GCA CTG GGC CGC TCC TTC CTG CAT GGA CCA GAG CTG GAC AAG GGG   389
Pro Ala Leu Gly Arg Ser Phe Leu His Gly Pro Glu Leu Asp Lys Gly
             80              85                       90

CAG CTA CGT ATC CAT CGT GAT GGC ATC TAC ATG GTA CAC ATC CAG GTG   437
Gln Leu Arg Ile His Arg Asp Gly Ile Tyr Met Val His Ile Gln Val
```

|                                       |     |
| ------------------------------------- | --- |
| ACG CTG GCC ATC TGC TCC TCC ACG ACG GCC TCC AGG CAC CAC CCC ACC<br>Thr Leu Ala Ile Cys Ser Ser Thr Thr Ala Ser Arg His His Pro Thr<br>110             115              120              125 | 485 |
| ACC CTG GCC GTG GGA ATC TGC TCT CCC GCC TCC CGT AGC ATC AGC CTG<br>Thr Leu Ala Val Gly Ile Cys Ser Pro Ala Ser Arg Ser Ile Ser Leu<br>              130              135              140 | 533 |
| CTG CGT CTC AGC TTC CAC CAA GGT TGT ACC ATT GTC TCC CAG CGC CTG<br>Leu Arg Leu Ser Phe His Gln Gly Cys Thr Ile Val Ser Gln Arg Leu<br>              145              150              155 | 581 |
| ACG CCC CTG GCC CGA GGG GAC ACA CTC TGC ACC AAC CTC ACT GGG ACA<br>Thr Pro Leu Ala Arg Gly Asp Thr Leu Cys Thr Asn Leu Thr Gly Thr<br>          160              165              170 | 629 |
| CTT TTG CCT TCC CGA AAC ACT GAT GAG ACC TTC TTT GGA GTG CAG TGG<br>Leu Leu Pro Ser Arg Asn Thr Asp Glu Thr Phe Phe Gly Val Gln Trp<br>175              180              185 | 677 |
| GTG CGC CCC TGA<br>Val Arg Pro<br>190 | 689 |

( 2 ) INFORMATION FOR SEQ ID NO:10:

( i ) SEQUENCE CHARACTERISTICS:
( A ) LENGTH: 216 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Phe His Val Ser Phe Arg Tyr Ile Phe Gly Ile Pro Pro Leu Ile
-24             -20             -15             -10

Leu Val Leu Leu Pro Val Thr Ser Ser Asp Arg Met Lys Gln Ile Glu
              -5               1               5

Asp Lys Ile Glu Glu Ile Leu Ser Lys Ile Tyr His Ile Glu Asn Glu
    10              15              20

Ile Ala Arg Ile Lys Lys Leu Ile Gly Glu Arg Thr Ser Gln Arg Phe
25              30              35              40

Ala Gln Ala Gln Gln Leu Pro Leu Glu Ser Leu Gly Trp Asp Val
            45              50              55

Ala Glu Leu Gln Leu Asn His Thr Gly Pro Gln Gln Asp Pro Arg Leu
            60              65              70

Tyr Trp Gln Gly Gly Pro Ala Leu Gly Arg Ser Phe Leu His Gly Pro
        75              80              85

Glu Leu Asp Lys Gly Gln Leu Arg Ile His Arg Asp Gly Ile Tyr Met
    90              95              100

Val His Ile Gln Val Thr Leu Ala Ile Cys Ser Ser Thr Thr Ala Ser
105             110             115             120

Arg His His Pro Thr Thr Leu Ala Val Gly Ile Cys Ser Pro Ala Ser
            125             130             135

Arg Ser Ile Ser Leu Leu Arg Leu Ser Phe His Gln Gly Cys Thr Ile
            140             145             150

Val Ser Gln Arg Leu Thr Pro Leu Ala Arg Gly Asp Thr Leu Cys Thr
        155             160             165

Asn Leu Thr Gly Thr Leu Leu Pro Ser Arg Asn Thr Asp Glu Thr Phe
    170             175             180

Phe Gly Val Gln Trp Val Arg Pro
```

CD27 LIGAND

CROSS REFERENCE TO RELATED APPLICATION

This application is a continuation-in-part application of U.S. patent application Ser. No. 07/941,648, filed Sep. 8, 1992, now abandoned.

BACKGROUND OF THE INVENTION

The lymphocyte antigen CD27 is a cytokine receptor found on the surface of most human T lymphocytes and some B lymphocytes. A cDNA encoding the CD27 receptor has been isolated (Camerini et al., *J. Immunol.* 147:3165, (1991). Based on the predicted polypetide sequence, CD27 belongs to a family of cysteine-rich receptors whose known ligands include nerve growth factor, and TNF-$\alpha$ and -$\beta$. Structural similarities suggest that CD27 belongs to a lymphocyte-specific subgroup of the family comprised of the B cell Ag CD40, the rat T cell subset Ag OX40, and the mouse T cell activation Ag 4-1BB. The CD27 receptor is believed to mediate functions which allow survival of activated cells.

The growth factor responsible for binding to and initiating CD27 activities has not yet been identified. The existence and nature of such growth factors will be important in elucidating mechanisms for survival of activated cells. A need has thus existed for identifying and characterizing a ligand that binds to CD27.

SUMMARY OF THE INVENTION

The present invention provides a novel CD27 ligand (CD27L) that binds to the CD27 receptor. The present invention also provides isolated DNA encoding the CD27L protein, expression vectors comprising the isolated DNA, and a method for producing CD27L by cultivating host cells containing the expression vectors under conditions appropriate for expression of the CD27L protein. Antibodies directed against the CD27L protein or an immunogenic fragment thereof are also disclosed.

BRIEF DESCRIPTION OF THE DRAWINGS

In FIG. 1, purified T cells ($1 \times 10^5$/well) were cultured with a titration of fixed CV-1/EBNA cells which were transfected with either empty vector (o) or with vector expressing CD27L (●) for 3 days in the presence of a sub-optimal concentration of PHA (0.1% ). During the final 8 hrs of culture the cells were pulsed with $^3$H-thymidine and incorporation was determined. Each point represents the mean cpm ±SD of triplicate cultures. FIG. 1 thus shows that cells expressing CD27L (●) induce T cells to proliferate to a greater extent than cells expressing empty vector (o).

In FIGS. 2 and 3, purified CD4$^+$ or CD8$^+$ T cells ($1 \times 10^5$/well) were cultured with IL-2 (10 ng/ml) or CV-1/EBNA cells expressing CD27L ($1 \times 10^4$/well) for 3 days with sub-optimal PHA. Cells were cultured either with (hatched columns) or without (open columns) a neutralizing IL-2 antiserum. FIGS. 2 and 3 thus show that for both CD4$^+$ and CD8$^+$ T cells CD27L stimulates proliferation in an IL-2 independent manner.

FIG. 4 thus shows that cells expressing CD27L (■) have no stimulatory effect on cytolytic activity in the absence of costimulation. In contrast, FIG. 5 shows that cells expressing CD27L (■) which are costimulated with PHA enhance generation of cytolytic cells.

DETAILED DESCRIPTION OF THE INVENTION

Figure 1:
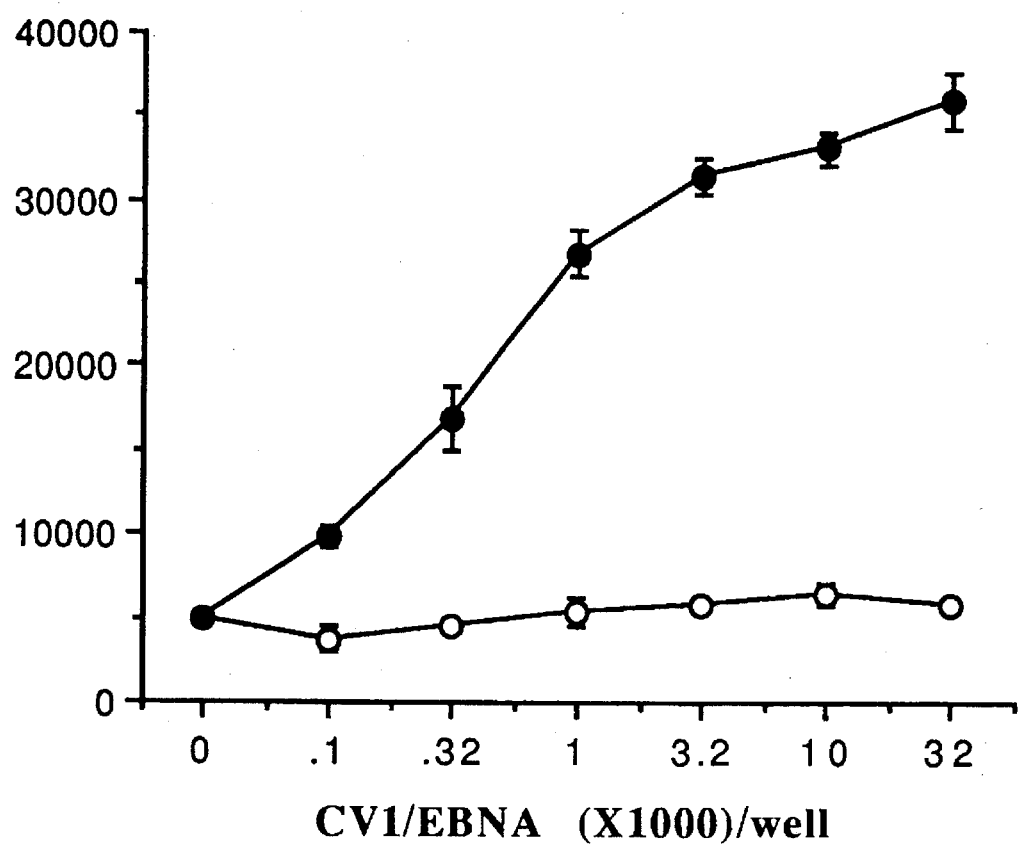
FIGS. 1–3 show that CD27L stimulates proliferation of purified human peripheral blood T cells (as described in detail in Example 8A.

A cDNA encoding a novel protein ligand for the T cell activation antigen CD27 has been isolated in accordance with the present invention. Also provided are expression vectors comprising the CD27 ligand (CD27L) cDNA and methods for producing recombinant CD27L polypeptides by cultivating host cells containing the expression vectors under conditions appropriate for expression of CD27L, and recovering the expressed CD27L. Purified CD27L protein is also encompassed by the present invention.

The present invention also provides CD27L or antigenic fragments thereof that can act as immunogens to generate antibodies specific to the CD27L immunogens. Monoclonal antibodies specific for CD27L or antigenic fragments thereof thus can be prepared.

The novel cytokine disclosed herein is a ligand for CD27, a receptor that is a member of the TNF/NGF receptor superfamily. CD27L is therefore believed to be the ligand that initiates the biological signal mediated by CD27, which is known to be expressed on the surface of most T cells and some B cells. One use of the CD27 ligand of the present invention is as a research tool for studying the role of CD27L in the survival of activated cells. The CD27L polypeptides of the present invention also may be employed in in vitro assays for detection of CD27 or CD27L or the interactions thereof. CD27L has been shown to induce the proliferation of costimulated T cells and enhance the generation of cytolitic T cells, suggesting that CD27L plays a role in the maturation of T cells. Biological studies of the CD27L of the present invention (as described in Examples 6, 8 and 10) show that CD27L costimulates T cell proliferation and also enhances generation of cytolytic T cell precursors.

The term "CD27L" as used herein refers to a genus of polypeptides which are capable of binding CD27. Human CD27L is within the scope of the present invention, as are CD27L proteins derived from other mammalian species. As used herein, the term "CD27L" includes membrane-bound proteins (comprising a cytoplasmic domain, a transmembrane region, and an extracellular domain) as well as truncated proteins that retain the CD27-binding property. Such truncated proteins include, for example, soluble CD27L comprising only the extracellular (receptor binding) domain.

The cDNA sequence and predicted amino acid sequence of CD27L is set forth in SEQ ID NO: 1 and SEQ ID NO: 2.

Isolation of a cDNA encoding human CD27L is described in Examples 1–4 below. A human CD27/Fc fusion protein was prepared as described in Example 1 for use in screening clones in a direct expression cloning procedure, to identify those expressing a protein that binds CD27.

Any of the cell lines that demonstrate binding of CD27 to CD27L may be used as a source of nucleic acid in an attempt to isolate a CD27L-encoding DNA sequence. A cDNA library may be prepared, for example, from the cell line U937, the monocytic cell line THP-1, the early pre-B lymphoblastic leukemia cell line EU-1, purified tonsillar T cells or MP-1 cells, and screened to identity CD27L cDNA using the direct expression cloning strategy described below. The cells may be derived from human, murine, or other mammalian sources, including but not limited to rat, bovine, porcine, or various primate cells.

Briefly, total RNA was extracted from MP-1 cells and enriched for poly(A)+ RNA by oligo(dT) cellulose chromatography, essentially as described by Ausubel et al., eds., *Current Protocols in Molecular Biology*, Vol. 1 (1987). First strand cDNA was prepared using the total RNA as template. DNA encoding the extracellular domain of human CD27 was amplified by polymerase chain reaction (PCR) using primers based on the human CD27 sequence published by Camerini et al., supra., and the amplified DNA fragment was isolated. An expression vector comprising the CD27 extracellular domain DNA fused in-frame to the N-terminus of a human IgG1 Fc region DNA sequence was constructed and transfected into mammalian cells. The expressed protein was purified by a procedure that involved use of a protein G column (to which the Fc portion of the fusion protein binds).

The human B-cell line MP-1 that expresses CD27L was identified using a two-step screening assay in which the CD27/Fc fusion protein was bound to cells having CD27L, followed by $^{125}$I-mouse anti-human Fc antibody bound to the Fc portion of CD27/Fc fusion protein. A cDNA library was prepared from the human EBV-transformed B cell line MP-1. cDNA from this library (in a mammalian expression vector that also replicates in *E. coli*) was transfected into CV-1/EBNA-1 (mammalian) cells, for isolation of clones expressing a CD27-binding protein by using a direct expression cloning technique. The clones were screened using the two-step screening method involving CD27/Fc fusion protein bound to cells, followed by $^{125}$I-mouse anti-human Fc antibody bound to the Fc portion of CD27/Fc fusion protein. The recombinant vector isolated from the positive clone (murine CD27L cDNA in plasmid pDC303) was transformed into *E. coli* cells, deposited with the American Type Culture Collection on Aug. 18, 1992, and assigned accession no. ATCC 69052. The deposit was made under the terms of the Budapest Treaty.

Sequence analysis of the resulting clone revealed an insert of 813 bp with a single long open reading frame capable of encoding a protein of 193 amino acids. The amino-terminal 20 amino acids were followed by 18 hydrophobic amino acids (amino acids 21–38) that presumably function as a transmembrane anchor. This lack of a signal sequence, the presence of an internal hydrophobic domain, and the presence of two potential N-linked glycosylation sites (amino acids Asn$^{63}$ and Asn$^{170}$) in the C-terminal domain suggested that CD27L is a type II transmembrane protein having an extracellular carboxy-terminal domain.

The originally isolated cDNA clone contained only 37 nucleotides upstream of the presumed initiation codon (beginning with nucleotide 114 of SEQ ID NO: 1) with no in-frame termination codons. In addition, the sequence around this initiation site does not conform to the consensus for such sites described by Kozak, *Nucl. Acids. Res.* 12:857 (1984). Thus, an "anchored PCR" reaction (as described by Carrier et al., *Gene* 116:173 (1992)) was performed to clone the 5' end of the CD27L transcript to ensure that there was not an upstream initiation site. This resulted in the identification of an additional 113 nucleotides (nucleotides 1–113 of SEQ ID NO: 1 ) preceding the end of the originally isolated clone. No initiation sites were found upstream of that which was previously identified.

The human CD27L cDNA may be radiolabeled and used as a probe to isolate other mammalian CD27L cDNAs by cross-species hybridization. For example, a cDNA library prepared from activated murine peripheral blood lymphocytes may be screened with radio-labeled human cDNA to isolate a positive clone.

Although a CD27/Fc fusion protein was employed in the screening procedure described in Example 4 below, labeled CD27 can be used to screen clones and candidate cell lines for expression of CD27L proteins. The CD27/Fc fusion protein, however, offers the advantage of being easily purified. In addition, disulfide bonds form between the Fc regions of two separate fusion protein chains, creating dimers. The dimeric CD27/Fc receptor was chosen for the potential advantage of higher affinity binding of the CD27 ligand, in view of the possibility that the ligand being sought would be multimeric.

Further, other suitable fusion proteins comprising CD27 may be substituted for CD27/Fc in the screening procedures. Other fusion proteins can be made by fusing a DNA sequence for the ligand binding domain of CD27 to a DNA sequence encoding another polypeptide that is capable of affinity purification, for example, avidin or streptavidin. The resultant gene construct can be introduced into mammalian cells to express a fusion protein. Receptor/avidin fusion proteins can be purified by biotin affinity chromatography. The fusion protein can later be recovered from the column by eluting with a high salt solution or another appropriate buffer. Other antibody Fc regions may be substituted for the human IgG1 Fc region described in Example 1. Other suitable Fc regions are those that can bind with high affinity to protein A or protein G, and include the Fc region of murine IgG1 or fragments of the human IgG1 Fc region, e.g., fragments comprising at least the hinge region so that interchain disulfide bonds will form.

cDNA encoding a CD27L polypeptide may be isolated from other mammalian species using the methods disclosed in the examples. For example, a murine cDNA library may be substituted for the human cDNA library that was screened for binding of radioiodinated human CD27/Fc fusion protein in the direct expression cloning procedure described in Example 4. Clones expressing other mammalian CD27L proteins may thus be identified. Cell types from which cDNA libraries may be prepared may be chosen by the two-step binding procedure described in Example 2, or any other suitable technique. Alternatively, mRNAs isolated from various cell lines can be screened by Northern hybridization to determine a suitable source of mammalian CD27L mRNA for use in cloning a CD27L gene.

Alternatively, one can utilize the human CD27L cDNAs described herein to screen cDNA derived from other mammalian sources for CD27L cDNA using well-known cross-species hybridization techniques. Briefly, an oligonucleotide probe based on the nucleotide sequence of the coding region (preferably the extracellular region) of the murine or human clone is prepared by standard techniques. The murine or human probe is used to screen a mammalian cDNA library or genomic library, generally under moderately stringent conditions.

One embodiment of the present invention provides soluble CD27L polypeptides. Soluble CD27L polypeptides comprise all or part of the extracellular domain of a native CD27L but lack the transmembrane region that would cause retention of the polypeptide on a cell membrane. Soluble CD27L thus is secreted upon expression. The soluble CD27L polypeptides that may be employed retain the ability to bind the CD27 receptor. Soluble CD27L may also include part of the transmembrane region or part of the cytoplasmic domain or other sequences, provided that the soluble CD27L protein is capable of being secreted.

Soluble CD27L may be identified (and distinguished from its non-soluble membrane-bound counterparts) by separating intact cells which express the desired protein from the culture medium, e.g., by centrifugation, and assaying the medium (supernatant) for the presence of the desired protein. The culture medium may be assayed using procedures which are similar or identical to those described in the examples below. The presence of CD27L in the medium indicates that the protein was secreted from the cells and thus is a soluble form of the desired protein. Soluble CD27L may be a naturally-occurring form of this protein.

The use of soluble forms of CD27L is advantageous for certain applications. Purification of the proteins from recombinant host cells is facilitated, since the soluble proteins are secreted from the cells. Further, soluble proteins are generally more suitable for intravenous administration.

Soluble forms of CD27L proteins may also be prepared by deleting the transmembrane and intracytoplasmic domains, and adding an appropriate signal peptide to enable secretion of the soluble form of the protein (Smith et al., *Science* 238:1704, 1987; Treiger et al., *J. Immunol.* 136:4099, 1986). Soluble CD27L polypeptides include those comprising the entire or partial extracellular domain of a native CD27L protein. Truncated CD27L, including soluble polypeptides, may be prepared by any of a number of conventional techniques. In the case of recombinant proteins, a DNA fragment encoding a desired fragment may be subcloned into an expression vector. Alternatively, a desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to isolate a DNA sequence encoding a desired protein fragment.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

Soluble CD27L proteins may also be expressed as fusion proteins in which the extracellular domain of the membrane protein is joined to an immunoglobulin heavy chain constant region (Fanslow et al., *J. Immunol.* 149:65, 1992; Noelle et al., *Proc. Natl. Acad. Sci. U.S.A.* 89:6550, 1992) to create a dimeric soluble CD27L molecule, or may be fused with the extracellular domain of the murine T lymphocyte antigen CD8 (Hollenbaugh et al., *EMBO J.* 11:4313, 1992).

Multiple soluble CD27L molecules may also be oligomerized. A preferred method for creating multimeric forms of CD27L is to use a leucine zipper, which is a repetitive amino acid heptad motif present as a conserved domain in certain native proteins. The leucine zipper contains four to five leucine residues interspersed with other amino acids which fold as short, parallel coiled coils, and cause oligomerization of the proteins to which they are fused (O'Shea et al., *Science* 254:539; 1991). The general architecture of the parallel coiled coil has been well characterized, with a "knobs-into-holes" packing as proposed by Crick in 1953 (*Acta Crystallogr.* 6:689). Dimers formed by a leucine zipper domain are stabilized by the heptad repeat, designated (abcdefg)$_n$, according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical leucine zipper domains, the "knobs" formed by the hydrophobic side chains of the first helix are packed into the "holes" formed between the side chains of the second helix.

The leucine residues at position d contribute large hydrophobic stabilization energies, and are important for dimer formation (Krystek et al., *Int. J. Peptide Res.* 38:229, 1991). Lovejoy et al. recently reported the synthesis of a triple-stranded α-helical bundle in which the helices run up-up-down (*Science* 259:1288, 1993). Their studies confirmed that hydrophobic stabilization energy provides the main driving force for the formation of coiled coils from helical monomers and that electrostatic interactions contribute to the stoichiometry and geometry of coiled coils.

Leucine zipper sequences derived from the fos and jun proteins may be used in the formation of bispecific fusion proteins, as described by Kostelny et al., *J. Immunol.* 148:1547, 1992; O'Shea et al., *Science* 245:646, 1989; and Turner and Tjian, *Science* 243:1689, 1989. Leucine zipper domains are also found in the yeast transcription factor GCN4 and a heat-stable DNA-binding protein found in rat liver (C/EBP; Landschulz et al., *Science* 243:1681, 1989). The fusogenic proteins of several different viruses, including paramyxovirus, coronavirus, measles virus and many retroviruses, also possess leucine zipper motifs (Buckland and Wild, *Nature* 338:547,1989; Britton, *Nature* 353:394, 1991; Delwart and Mosialos, *AIDS Research and Human Retroviruses* 6:703, 1990). The leucine zipper domains in these fusogenic viral proteins are near the transmembrane region of the proteins, where the leucine zipper motifs may contribute to the oligomeric structure of the fusogenic proteins.

Several studies have indicated that conservative amino acids may be substituted for individual leucine residues with minimal decrease in the ability to dimerize. van Heekeren et al. reported that a number of different amino residues can be substituted for the leucine residues in the leucine zipper domain of GCN4, and that some GCN4 proteins containing two leucine substitutions were weakly active (*Nucl. Acids*

Res. 20:3721, 1992). Amino acid substitutions in the a and d residues of a synthetic peptide representing the GCN4 leucine zipper domain may also change the oligomerization of leucine zipper domains (Alber, Sixth Symposium of the Protein Society, San Diego, Calif.). When all residues at position a are changed to isoleucine, the leucine zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes.

The present invention provides purified CD27L polypeptides, both recombinant and non-recombinant. Variants and derivatives of native CD27L proteins that retain the desired biological activity are also within the scope of the present invention. CD27L variants may be obtained by mutations of nucleotide sequences coding for native CD27L polypeptides. A CD27L variant, as referred to herein, is a polypeptide substantially homologous to a native CD27L, but which has an amino acid sequence different from that of native CD27L (human, murine or other mammalian species) because of one or more deletions, insertions or substitutions.

The variant amino acid sequence preferably is at least 80% identical to a native CD27L amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identifies and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

CD27L also may be modified to create CD27L derivatives by forming covalent or aggregative conjugates with other chemical moieties, such as glycosyl groups, lipids, phosphate, acetyl groups and the like. Covalent derivatives of CD27L may be prepared by linking the chemical moieties to functional groups on CD27L amino acid side chains or at the N-terminus or C-terminus of a CD27L polypeptide or the extracellular domain thereof. Other derivatives of CD27L within the scope of this invention include covalent or aggregative conjugates of CD27L or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a CD27L polypeptide. The signal or leader peptide co-translationally or post-translationally directs transfer of the conjugate from its side of synthesis to a site inside or outside of the cell membrane or cell wall. CD27L polypeptide fusions can comprise peptides added to facilitate purification and identification of CD27L. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK), which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A murine hybridoma designated 4E11 produces a monoclonal antibody that binds the peptide DYKDDDDK in the presence of certain divalent metal cations (as described in U.S. Pat. No. 5,011,912) and has been deposited with the American Type Culture Collection under accession no HB 9259.

The present invention further includes CD27L polypeptides with or without associated native-pattern glycosylation. CD27L expressed in yeast or mammalian expression systems (e.g., COS-7 cells) may be similar to or significantly different from a native CD27L polypeptide in molecular weight and glycosylation pattern, depending upon the choice of expression system. Expression of CD27L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, N-glycosylation sites in the CD27L extracellular domain can be modified to preclude glycosylation while allowing expression of a homogeneous, reduced carbohydrate analog using yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain. Known procedures for inactivating N-glycosylation sites in proteins include those described in U.S. Pat. No. 5,071,972 and EP 276,846. In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein.

Naturally occurring CD27L variants are also encompassed by the present invention. Examples of such variants are proteins that result from alternative mRNA splicing events (since CD27L is encoded by a multi-exon gene) or from proteolytic cleavage of the CD27L protein, wherein the CD27-binding property is retained. Alternative splicing of mRNA may yield a truncated but biologically active CD27L protein, such as a naturally occurring soluble form of the protein, for example. Variations attributable to proteolysis include, for example, differences in the N- or C-termini upon expression in different types of host cells, due to proteolytic removal of one or more terminal amino acids from the CD27L protein.

Nucleic acid sequences within the scope of the present invention include isolated DNA and RNA sequences that hybridize to the CD27L nucleotide sequences disclosed herein under conditions of moderate or severe stringency, and which encode biologically active CD27L. Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press, (1989). Conditions of moderate stringency, as defined by Sambrook et al., include use of a prewashing solution of 5 X SSC, 0.5% SDS, 1.0 mM EDTA (pH 8.0) and hybridization conditions of about 55° C., 5 X SSC, overnight. Conditions of severe stringency include higher temperatures of hybridization and washing. The skilled artisan will recognize that the temperature and wash solution salt concentration may be adjusted as necessary according to factors such as the length of the probe.

The present invention thus provides isolated DNA sequences encoding biologically active CD27L, selected from: (a) DNA derived from the coding region of a native mammalian CD27L gene (e.g., cDNA derived from the coding region of the murine or human CD27L cDNA isolated as described in Examples 4; (b) DNA capable of hybridization to a DNA of (a) under moderately stringent conditions and which encodes biologically active CD27L; and (c) DNA which is degenerate as a result of the genetic code to a DNA defined in (a) or (b) and which encodes biologically active CD27L.

Variants possessing the requisite ability to bind CD27 may be identified by any suitable assay. Biological activity of CD27L may be determined, for example, by competition for binding to the ligand binding domain of CD27 (i.e. competitive binding assays).

One type of a competitive binding assay for CD27L polypeptide uses a radiolabeled, soluble human or murine CD27L and intact cells expressing cell surface CD27 (e.g., cell lines such as MP-1 described in Example 2). Instead of intact cells, one could substitute soluble CD27 (such as a CD27/Fc fusion protein) bound to a solid phase through a Protein A or Protein G interaction with the Fc region of the fusion protein. Another type of competitive binding assay utilizes radiolabeled soluble CD27 such as a CD27/Fc fusion protein, and intact cells expressing CD27L. Alternatively, soluble CD27L could be bound to a solid phase.

Competitive binding assays can be performed using standard methodology. For example, radiolabeled murine CD27L can be used to compete with a putative CD27L homolog to assay for binding activity against surface-bound CD27. Qualitative results can be obtained by competitive autoradiographic plate binding assays, or Scatchard plots may be utilized to generate quantitative results.

Competitive binding assays with intact cells expressing CD27 can be performed by two methods. In a first method, cells expressing cell surface CD27 are grown either in suspension or by adherence to tissue culture plates. Adherent cells can be removed by treatment with 5 mM EDTA treatment for ten minutes at 37° C. In a second method, transfected COS cells expressing membrane-bound CD27 can be used. COS cells or another mammalian cell, such as the CV-1/EBNA-1 cell line, can be transfected with human CD27 cDNA in an appropriate vector to express full length CD27 with an extracellular region.

Alternatively, soluble CD27 can be bound to a solid phase such as a column chromatography matrix or a similar substrate suitable for analysis for the presence of a detectable moiety such as $^{125}I$. Binding to a solid phase can be accomplished, for example, by obtaining a CD27/Fc fusion protein and binding it to a protein A or protein G-containing matrix.

The binding characteristics of CD27L (including variants) may also be determined using the conjugated, soluble CD27 (for example, $^{125}I$-CD27/Fc) in competition assays similar to those described above. In this case, however, intact cells expressing CD27L, or soluble CD27L bound to a solid substrate, are used to measure the extent to which a sample containing a putative CD27 variant competes for binding of a conjugated soluble CD27 to CD27L.

The CD27L of the present invention can be used in a binding assay to detect cells expressing CD27. For example, CD27L or an extracellular domain or a fragment thereof can be conjugated to a detectable moiety such as $^{125}I$. Radiolabeling with $^{125}I$ can be performed by any of several standard methodologies that yield a functional $^{125}I$-CD27L molecule labeled to high specific activity. Alternatively, another detectable moiety such as an enzyme that can catalyze a colorometric or fluorometric reaction, biotin or avidin may be used. Cells to be tested for CD27 expression can be contacted with conjugated CD27L. After incubation, unbound conjugated CD27L is removed and binding is measured using the detectable moiety.

CD27L polypeptides may exist as oligomers, such as dimers or trimers. Oligomers are linked by disulfide bonds formed between cysteine residues on different CD27L polypeptides. In one embodiment of the invention, a CD27L dimer is created by fusing CD27L to the Fc region of an antibody (IgG1) in a manner that does not interfere with binding of CD27L to the CD27 ligand binding domain. The Fc polypeptide preferably is fused to the N-terminus of a soluble CD27L (comprising only the extracellular domain). A procedure for isolating DNA encoding an IgG1 Fc region for use in preparing fusion proteins is presented in Example 1 below. A gene fusion encoding the CD27L/Fc fusion protein is inserted into an appropriate expression vector. The CD27L/Fc fusion proteins are allowed to assemble much like antibody molecules, whereupon interchain disulfide bonds form between Fc polypeptides, yielding divalent CD27L. If fusion proteins are made with both heavy and light chains of an antibody, it is possible to form a CD27L oligomer with as many as four CD27L extracellular regions. Alternatively, one can link two soluble CD27L domains with a peptide linker such as the Gly$_4$SerGly$_5$Ser linker sequence described in U.S. Pat. No. 5,073,627.

The present invention provides oligomers of CD27L extracellular domains or fragments thereof, linked by disulfide interactions, or expressed as fusion polymers with or without spacer amino acid linking groups. For example, a dimer CD27L molecule can be linked by an IgG Fc region linking group.

The present invention provides recombinant expression vectors for expression of CD27L, and host cells transformed with the expression vectors. Any suitable expression system may be employed. The vectors include a CD27L DNA sequence (a synthetic or cDNA-derived DNA sequence encoding a CD27L polypeptide) operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the CD27L DNA sequence. Thus, a promoter nucleotide sequence is operably linked to a CD27L DNA sequence if the promoter nucleotide sequence controls the transcription of the CD27L DNA sequence. The ability to replicate in the desired host cells, usually conferred by an origin of replication, and a selection gene by which transformants are identified, may additionally be incorporated into the expression vector.

In addition, sequences encoding appropriate signal peptides that are not native to the CD27L gene can be incorporated into expression vectors. For example, a DNA sequence for a signal peptide (secretory leader) may be fused in frame to the CD27L sequence so that the CD27L is initially translated as a fusion protein comprising the signal peptide. A signal peptide that is functional in the intended host cells enhances extracellular secretion of the CD27L polypeptide. The signal peptide is cleaved from the CD27L polypeptide upon secretion of CD27L from the cell.

Suitable host cells for expression of CD27L polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce CD27L polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a CD27L polypeptide may include an N-terminal methionine residue to facilitate expression of the recombinant polypeptide in the prokaryotic host cell. The N-terminal Met may be cleaved from the expressed recombinant CD27L polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a CD27L DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., U.S.A.).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ P$_L$ promoter and a cI857ts thermolabile repressor sequence. Plasmid vectors available from the American Type Culture Collection which incorporate derivatives of the λ P$_L$ promoter include plasmid pHUB2 (resident in *E. coli* strain JMB9 (ATCC 37092)) and pPLc28 (resident in *E. coli* RR1 (ATCC 53082)).

CD27L alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the CD27L polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al.,

*Proc. Natl. Acad. Sci. USA* 75:1929, 1978. The Hinnen et al. protocol selects for Trp⁺ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian or insect host cell culture systems could also be employed to express recombinant CD27L polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. For expression of a type II protein lacking a native signal sequence, a heterologous signal sequence may be added, such as the signal sequence for interleukin-7 (IL-7) described in U.S. Pat. No. 4,965,195, or the signal sequence for interleukin-2 receptor described in U.S. patent application Ser. No. 06/626,667 filed on Jul. 2, 1984.

The present invention provides substantially homogeneous CD27L protein, which may be produced by recombinant expression systems as described above or purified from naturally occurring cells. The CD27L is purified to substantial homogeneity, as indicated by a single protein band upon analysis by SDS-polyacrylamide gel electrophoresis (SDS-PAGE).

In one embodiment of the present invention, CD27L is purified from a cellular source using any suitable protein purification technique. The cells may, for example, be activated T-lymphocytes from a mammalian species of interest, such as the murine cell line 7B9 described in examples 2 and 3 or induced human peripheral blood T-cells.

An alternative process for producing the CD27L protein comprises culturing a host cell transformed with an expression vector comprising a DNA sequence that encodes CD27L under conditions such that CD27L is expressed. The CD27L protein is then recovered from culture medium or cell extracts, depending upon the expression system employed. As the skilled artisan will recognize, procedures for purifying the recombinant CD27L will vary according to such factors as the type of host cells employed and whether or not the CD-30-L is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify CD27L. Some or all of the foregoing purification steps, in various combinations, can be employed to provide a substantially homogeneous recombinant protein.

It is also possible to utilize an affinity column comprising the ligand binding domain of CD27 to affinity-purify expressed CD27L polypeptides. CD27L polypeptides can be removed from an affinity column in a high salt elution buffer and then dialyzed into a lower salt buffer for use. Alternatively, the affinity column may comprise an antibody that binds CD27L. Example 5 describes a procedure for employing the CD27L protein of the present invention to generate monoclonal antibodies directed against CD27L.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express CD27L as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

The present invention further provides antisense or sense oligonucleotides comprise a single-stranded nucleic acid sequence (either RNA or DNA) capable of binding to target CD27L mRNA (sense) or CD27L DNA (antisense) sequences. Antisense or sense oligonucleotides, according to the present invention, comprise a fragment of the coding region of CD27L cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of CD27L proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence. Antisense or sense oligonucleotides may be introduced into a cell containing the target nucleic acid sequence by any gene transfer method., including, for example, $CaPO_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT Application U.S. 90/02656). Alternatively, other promotor sequences may be used to express the oligonucleotide.

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate particular embodiments and not to limit the scope of the invention.

EXAMPLE 1

Preparation of Soluble CD27/Fc Fusion Protein

This example describes construction of a vector encoding CD27/Fc that expresses a soluble CD27/Fc fusion protein for use in detecting cDNA clones encoding a CD27 ligand (CD27L). A cDNA fragment encoding the extracellular region (ligand binding domain) of the human receptor CD27 was obtained using polymerase chain reaction (PCR) techniques, and is based upon the sequence published by Camerini et al., *J. Immunol.* 147:3165, 1991.

The CD27 cDNA used as a template in the PCR reaction was obtained from D. Camerini and used as a template in the PCR reaction. The 5' primer employed in the PCR reaction was a single-stranded oligonucleotide (27-mer) having the following sequence:

SEQ ID NO: 3: 5'-ATAGCGGCCGCCTGGGCAGGGACCATG-3'

This primer comprises a recognition site for the restriction endonuclease NotI (underlined) upstream of a sequence containing nucleotides 83–103 of the CD27 sequence published by Camerini et al., up to the N-terminal methionine (encoded by the translation initiation codon ATG).

The 3' primer employed in the PCR reaction was a single-stranded oligonucleotide (39-mer) of the sequence:

SEQ ID NO: 4: 3'-GTGACCGGTGGGGTTTCTAGGGAC-CTCGGGTCTAGAGCG-5'

This primer comprises a sequence (bold type) that is complementary to nucleotides 629-652 (which encode amino acids 157–164) of the CD27 sequence published by Camerini et al. This primer was designed to eliminate the last 7 amino acids of the extracellular domain of CD27. The sequence CTCGGG that follows the CD27 sequence is complementary to codons for Glu and Pro. Glu and Pro are the first two amino acids of an antibody Fc fragment that is fused to the C-terminus of the CD27 fragment as described below. The primer also positions a recognition site for the restriction endonuclease BglII (underlined) downstream, for use in attaching a DNA sequence encoding the remainder of the Fc-encoding gene.

The PCR reaction may be conducted using any suitable procedure, such as those described in Sarki et al., *Science* 239:487 (1988); in *Recombinant DNA Methodology*, Wu et al., eds., Academic Press Inc., San Diego (1989), pp. 189–196; and in *PCR Protocols: A Guide to Methods and Applications*, Innis et al., eds., Academic Press, Inc. (1990). An example of a suitable PCR procedure is as follows. All temperatures are in degrees centigrade. The following PCR reagents are added to a 0.5 ml Eppendorf microfuge tube: 10 μl of 10X PCR buffer (500 mM KCl, 100 mM Tris-HCl, pH 8.3 at 25° C., 25 mM $MgCl_2$, and 1 mg/ml gelatin) (Perkins-Elmer Cetus, Norwalk, Conn.), 8 μl of a 2.5 mM solution containing each dNTP (2 mM dATP, 2 mM dCTP, 2 mM dGTP and 2 mM dTTP), 2.5 units (0.5 μl of standard 5000 units/ml solution) of Taq DNA polymerase (Perkins-Elmer Cetus), 1 ng of template DNA, 100 picomoles of each of the oligonucleotide primers, and water to a final volume of 100 μl. The final mixture is then overlaid with 100 gl parafin oil. PCR is carded out using a DNA thermal cycler (Ericomp, San Diego, Calif.).

In a preferred procedure, the template was denatured at 94° for 5 minutes, followed by 5 cycles of 94° for 1 minute (denaturation), 50° for 1 min. (annealing), and 72° for 1 min. (extension); followed by 30 cycles of 94° for 1 min., 60° for 1 min., and 72° for 1 min., with the last cycle being followed by a final extension at 72° for 7 minutes. An aliquot of the products of this PCR reaction was reamplified in a second PCR reaction, using the same conditions.

The desired DNA fragment amplified by this PCR reaction comprised a NotI site upstream of a sequence encoding the extracellular domain of CD27 (but deleting the last seven amino acids in order to remove the Cys amino acid), followed by a BglII site. The PCR reaction products were digested with NotI and BglII, and the desired fragment was purified by gel electrophoresis. The removal of the Cys amino acid was necessary in order to facilitate expression of the CD27/Fc fusion protein described below.

A DNA sequence encoding an antibody Fc fragment, to be fused to the CD27-encoding DNA fragment, was prepared as follows. DNA encoding a single chain polypeptide derived from the Fc region of a human IgG1 antibody has been cloned into the SpeI site of the pBLUESCRIPT SK® vector, which is commercially available from Stratagene Cloning Systems, La Jolla, Calif. This plasmid vector is replicable in *E. coli* and contains a polylinker segment that includes 21 unique restriction sites. A unique BglII site was introduced near the 5' end of the inserted Fc encoding sequence.

The Fc polypeptide encoded by the DNA extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate CD27/Fc fusion proteins, forming dimers as discussed above.

The recombinant vector containing the Fc sequence is digested with BglII (which cleaves only at the 5' end) and NotI (which cleaves the vector in the multiple cloning site downstream of the Fc cDNA insert). The Fc-encoding fragment (about 720 bp in length) was isolated by conventional procedures using LMT agarose gel electrophoresis.

The NotI/BglII CD27-encoding DNA fragment and the BglII/Nod Fc-encoding DNA fragment prepared above were ligated into an expression vector designated pDC406 as follows. Plasmid pDC406, which has been described by McMahan et al. (*EMBO J.* 10:2821, 1991), is an expression vector for use in mammalian cells, but is also replicable in *E. coli* cells.

pDC406 contains origins of replication derived from SV40, Epstein-Barr virus and pBR322 and is a derivative of HAV-EO described by Dower et al., *J. Immunol.* 142:4314 (1989). pDC406 differs from HAV-EO by the deletion of the intron present in the adenovirus 2 tripartite leader sequence in HAV-EO. pDC406 was digested with NotI, which cleaves the plasmid in a multiple cloning site just 3' of the SalI site, then treated with calf intestine alkaline phosphatase (CIAP) to prevent self ligation.

A three-way ligation to join the vector, Fc, and CD27 DNA fragments was conducted under conventional conditions, and *E. coli* cells were transformed with the ligation mixture. A plasmid of the desired size that was recovered from the *E. coli* cells was found to comprise the CD27/Fc gene fusion insert, but in the wrong orientation for expression. The CD27/Fc gene fusion was excised from this recombinant plasmid by NotI digestion and ligated to Nod-digested and CIAP-treated pDC406. *E. coli* cells were transformed with the ligation mixture. A recombinant plasmid containing the insert in the desired orientation was isolated. The CD27 sequence was fused (in the same reading frame) to the downstream Fc sequence.

CD27/Fc fusion molecules preferably are synthesized in recombinant mammalian cell culture because they are generally too large and complex to be synthesized by prokaryotic expression methods. Examples of suitable mammalian cells for expressing a receptor/Fc fusion protein include CV-1 cells (ATCC CCL 70) and COS-7 cells (ATCC CRL 1651), both derived from monkey kidney.

The DNA construct pDC406/CD27/Fc was transfected into the monkey kidney cell line CV-1/EBNA-1 (ATCC CRL 10478). In mammalian host cells such as CV-1/EBNA-1, the CD27/Fc fusion protein is expressed off the HIV transactivating region (TAR) promoter. The CV-1/EBNA-1 cell line was derived by transfection of the CV-1 cell line (ATCC CCL 70) with a gene encoding Epstein-Barr virus nuclear antigen-1 (EBNA-1) that constitutively expresses EBNA-1 driven from the human CMV intermediate-early enhancer/promoter as described by McMahan et al., supra. The EBNA-1 gene allows for episomal replication of expression vectors, such as pDC406, that contain the EBV origin of replication.

CV-1/EBNA-1 cells transfected with the pDC406/CD27/Fc vector were cultivated in roller bottles to allow transient expression of the fusion protein, which is secreted into the culture medium via the CD27 signal peptide. The CD27/Fc fusion protein was purified by affinity chromatography. Briefly, one liter of culture supernatant containing the CD27/Fc fusion protein was purified by filtering the supernatants (e.g., in a 0.45μ filter) and applying the filtrate to a protein G affinity column (Schleicher and Schuell, Keene, N.H.) according to manufacturer's instructions. The Fc portion of the fusion protein is bound by the Protein G on the column. Bound fusion protein was eluted from the column and the purity confirmed on a silver stained SDS gel.

EXAMPLE 2

Screening of Cell Lines for Binding of CD27

This example describes screening of certain cell lines for the ability to bind a CD27/Fc fusion protein. The screening assay used was a two-step method involving CD27/Fc fusion protein bound to cells, followed by $^{125}$I-mouse anti-human Fc antibody bound to the Fc portion of CD27/Fc fusion protein. Those cell lines found to be capable of binding CD27/Fc were considered to be candidates for use as nucleic acid sources in the attempt to clone CD27L.

The mouse anti-human Fc antibody was obtained from Jackson Laboratories. This antibody showed minimal binding to Fc proteins bound to the Fcγ receptor. The antibody was labeled using the Chloramine T method. Briefly, a P6 column was prepared according to the manufacturer's instructions. In a microfuge tube, 10 μg of antibody was dissolved in 10 μl of PBS. 2000 μCi of carrier-free Na$^{125}$I was added and the solution was mixed well. 15 μl of a freshly prepared solution of chloramine-T (32 μg/ml in 0.05M sodium phosphate buffer (pH 7.2)) was then added and the mixture was incubated for 30 minutes at room temperature. The mixture was immediately applied to the P6 column. The radiolabelled antibody was then eluted from the column by collecting 100–150 μl fractions of eluate. Binding media was added to peak fractions to bring the total volume of each fraction to 2 ml. Radioiodination yielded specific activities in the range of $5-10\times10^{15}$ cpm/mmol protein.

The MP-1 cell line was generated for use in screening for binding of CD27/Fc. MP-1 is a spontaneous Epstein Bart virus (EB V)-transformed B lymphoblastoid cell line grown out from peripheral blood mononuclear cells derived from a normal donor. After two weeks, proliferating B cells were subjected to two rounds of cloning at 0.3 cells per well in RPMI medium supplemented with 10% heat inactivated fetal bovine serum, 100 U/ml penicillin and 100 μg/ml streptomycin. MP-1 cells are derived from one such clone.

The MP-1 cell line was screened for binding of CD27/Fc by the following procedure. Approximately $2\times10^6$ cells were cultured in 96-well plates. 5 ml binding medium (RPMI 1640 containing 25 mg/ml bovine serum albumin (BSA), 2 mg/ml sodium azide, 20 mM Hepes pH 7.2) was added to the cells and and the cells were then incubated in the presence or absence of CD27/Fc for 1 hour at 37° C. with gentle agitation. The cells were sedimented from the mixture by centrifugation of the 96-well plates, washed with PBS, centrifuged again, and resuspended in binding medium. The cells were then incubated with the $^{125}$I-mouse anti-human Fc antibody, prepared as described above, for 1 hour at 37° C. Cells were also incubated with $^{125}$I-mouse anti-human Fc antibody in the presence of excess unlabelled anti-human Fc antibody as a negative control. Following a one hour incubation with the $^{125}$I-antibody, cells and unbound $^{125}$I-antibody were separated by the phthalate oil separation method, essentially as described by Dower et al., *J. Immunol.* 132:751, 1984. Cell-bound and free $^{125}$I-antibody were quantitated on a Packard Autogamma counter. MP-1 cells possessed significant numbers of CD27L bound to the cell surface, suggesting that the MP-1 cells may be a suitable source of mRNA for cloning CD27L cDNA.

EXAMPLE 3

Construction of cDNA Library

This example describes preparation of a cDNA library from human MP-1 B cells for expression cloning of human CD27L. The library construction technique was substantially similar to that described by Ausubel et al., eds., *Current Protocols In Molecular Biology*, Vol. 1, (1987). In general, total RNA was extracted from 8M guanidine HCl-lysed MP-1 cell cultures using differential ethanol precipitation and poly $(A)^+$ mRNA was isolated and enriched by oligo dT cellulose chromatography.

Double-stranded dDNA was made from an RNA template substantially as described by Gubler et al., *Gene* 25:263, 1983. Poly$(A)^+$ mRNA fragments were converted to RNA-cDNA hybrids using reverse transcriptase primed with random hexanucleotides. The RNA-cDNA hybrids were then converted into double-stranded cDNA fragments using RNAase H in combination with DNA polymerase I. The resulting double-stranded cDNA was blunt-ended with T4 DNA polymerase.

The following unkinased (i.e. unphosphorylated) BglII adaptors

SEQ ID NO: 5: 5'-GATCTTGGAACGAGACGACCTGCT-3' (24-mer)

SEQ ID NO: 6: 3'-AACCTTGCTCTGCTGGACGA-5' (20-mer)

were ligated to 5' ends of the above blunt-ended cDNA duplexes, using the adaptor cloning method described in Haymerle et al., *Nucleic Acids Res.* 14:8615, 1986. Under the described conditions, only the 24-mer oligonucleotide (top strand) will covalently bond to the cDNA during the ligation reaction. The non-covalently bound adaptors (including the complementary 20-mer oligonucleotide described above and any unligated adaptors) were removed by gel filtration chromatography at 65° C., leaving 24 nucleotide non-self-complementary overhangs on the cDNA termini.

The adaptored cDNA was inserted into pDC303, a mammalian expression vector that also replicates in *E. coli*. pDC303 was assembled from pDC201 (a derivative of pMLSV, previously described by Cosman et al., *Nature* 312: 768, 1984), SV40 and cytomegalovirus DNA and comprises, in sequence with the direction of transcription from the origin of replication, the following components: (1) SV40 sequences from coordinates 5171–270 containing the origin of replication, enhancer sequences and early and late promoters; (2) cytomegalovirus promoter and enhancer regions (nucleotides 671–63 from the sequence published by Boechart et al. (*Cell* 41:521, 1985); (3) adenovirus-2 from coordinates 5779–6079 containing the first exon of the tripartite leader (TPL), segment 7101–7172 and 9634–9693 containing the second exon and part of the third exon of the TPL and a multiple cloning site (MCS) containing sites for XhoI, KpnI, SmaI and Bg/I; (4) SV40 segments from coordinates 4127–4100 and 2770–2533 containing the polyadenylation and termination signals for early transcription; (5) adenovirus-2 sequences from coordinates 10532–11156 of the virus-associated RNA genes VAI and VAII of pDC201; and (6) pBR322 sequences from coordinates 4363–2486 and 1094–375 containing the ampicillin resistance gene and origin of replication.

The MP-1 cDNA library in pDC303 was introduced into *E. coli* strain DH10B by electroporation. Recombinants were plated to provide approximately 5,000 colonies per plate. These recombinants were pooled to give a bulk stock of approximately 500,000 recombinants for screening.

Aliquots of this bulk stock were plated to yield pools of 1000 colonies. Plasmid DNA was isolated from these pools and transfected into a sub-confluent layer of CV-1/EBNA-1 cells using DEAE-dextran followed by chloroquine treatment, similar to that described by Luthman et al., Nucl. Acids Res. 11:1295 (1983) and McCutchan et al., J. Natl. Cancer Inst. 41:351 (1986). The CV-1/EBNA-1 cells were derived as follows. The CV-1/EBNA-1 cell line constitutively expresses EBV nuclear antigen-1 driven from the CMV immediate-early enhancer/promoter. The African Green Monkey kidney cell line, CV-1 (ATCC CCL 70, was cotransfected with 5 μg of pSV2gpt (Mulligan & Berg, *Proc. Natl. Acad. Sci. USA* 78:2072, 1981) and 25 ug of pDC303/EBNA-1 using a calcium phosphate coprecipitation technique (Ausubel et al., eds., *Current Protocols in Molecular Biology*, Wiley, New York, 1987). pDC303/EBNA-1 was constructed from pDC302 (Mosley et al., *Cell* 59:335, 1989) in two steps. First, the intron present in the adenovirus tripartite leader sequence was deleted by replacing a PvuII to ScaI fragment spanning the intron with the following synthetic oligonucleotide pair to create plasmid pDC303:

SEQ ID NO: 7: 5'CTGTTGGGCTCGCGGTTGAGGA-
CAAACTCTTCGCGGTCTTTCCAGT-3'

SEQ ID NO: 8: 3'GACAACCCGAGCGCCAACTCCT-
GTTTGAGAAGCGCCAGAAAGGTCA-5'

Second, a HindIII-AhaII restriction fragment encoding Epstein-Barr virus nuclear antigen I (EBNA-1), and consisting essentially of EBV coordinates 107,932 to 109,894 (Baer et al., *Nature* 310:207, 1984), was then inserted into the multiple cloning site of pDC303 to create the plasmid pDC303/EBNA-1. The transfected cells were grown in the presence of hypoxanthine, aminopterin, thymidine, xanthine, and mycophenolic acid according to standard methods (Ausubel et al., supra; Mulligan & Berg, supra) to select for the cells that had stably incorporated the transfected plasmids. The resulting drug resistant colonies were isolated and expanded individually into cell lines for analysis. The cell lines were screened for the expression of functional EBNA-1. One cell line, clone 68, was found to express EBNA-1 using this assay, and was designated CV-1/EBNA-1.

In order to transfect the CV-1/EBNA-1 cells with the cDNA library, the cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of $2 \times 10^5$ cells/well on single-well chambered slides (LaboTek). Slides were pretreated with 1 ml human fibronectin (10 ug/ml in PBS) for 30 minutes followed by 1 wash with PBS. Media was removed from the adherent cell layer and replaced with 1.5 ml complete medium containing 66.6 µM chloroquine sulfate. 0.2 mls of DNA solution (2 µg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2.5 to 20 minutes followed by replacement of the solution with fresh complete medium. The cells were grown in culture to permit transient expression of the inserted sequences. These conditions led to an 80% transfection frequency in surviving CV-1/EBNA-1 cells.

EXAMPLE 4

Isolation of Human CD27L cDNA

The transfected cells were cultured for two to three days on chambered glass slides (Lab-Tek) to permit transient expression of the inserted DNA sequences. Transfected monolayers of CV-1/EBNA-1 cells were assayed for expression of CD27L by binding $^{125}$I-mouse anti-human Fc antibody by slide autoradiography as described below.

Transfected CV-1/EBNA-1 cells (adhered to chamber slides) were washed once with binding medium with nonfat dry milk (BM-NFDM) (RPMI medium 1640 containing 25 mg/ml bovine serum albumin (BSA), 2 mg/ml sodium azide, 20 mM HEPES, pH 7.2, and 50 mg/ml nonfat dry milk). Cells were then incubated with CD27/Fc in BM-NFDM (1 µg/ml) containing for 1 hour at room temperature. After incubation, the cell monolayers in the chambered slides were washed three times with BM-NFDM to remove unbound CD27/Fc fusion protein and then incubated with 40 ng/ml $^{125}$I-mouse anti-human Fc antibody (a 1:50 dilution) for 1 hour at room temperature. The cells were washed three times with BM-NFDM, followed by 2 washes with phosphate-buffered saline (PBS) to remove unbound $^{125}$I-mouse anti-human Fc antibody. The cells were fixed by incubating for 30 minutes at room temperature in 2.5% glutaraldehyde in PBS, pH 7.3, washed twice in PBS and air dried. The chamber slides containing the cells were exposed on a phophorimager overnight, then dipped in Kodak GTNB-2 photographic emulsion (6× dilution in water) and exposed in the dark for 3–5 days at 4° C. in a light proof box. The slides were then developed for approximately 4 minutes in Kodak D 19 developer (40 g/500 ml water), rinsed in water and fixed in Agfa G433C fixer. The slides were individually examined with a microscope at 25–40× magnification and positive cells expressing CD27L were identified by the presence of autoradiographic silver grains against a light background.

Using the slide autoradiography approach, approximately 50,000 cDNAs were screened in pools of approximately 1,000 cDNAs until assay of one transfectant pool showed multiple cells clearly positive for CD27/Fc binding. This pool was then partitioned into pools of 300 and again screened by slide autoradiography and a positive pool was identified. Individual colonies from this pool of 300 were screened until a single clone (clone #60) was identified which directed synthesis of a surface protein with detectable CD27/Fc binding activity. This clone was isolated, and its insert was sequenced to determine the sequence of the human CD27L cDNA clone 60.

The mammalian expression vector pDC304 containing human CD27L (designated pDC304/HuCD27L) was deposited with the American Type Culture Collection, Rockville, Md., U.S.A. (ATCC) on Aug. 18, 1992 and assigned accession number ATCC 69052. The deposit was made under the terms of the Budapest Treaty. The attached Sequence Listing sets forth the nucleotide (SEQ ID NO: 1) and predicted amino acid sequences of clone 60 (SEQ ID No: 1 and SEQ ID NO: 2) and associated information appears at the end of the specification immediately prior to the claims.

Sequence analysis of the resulting clone revealed an insert of 813 bp with a single long open reading frame capable of encoding a protein of 193 amino acids (SEQ ID NO: 1). The amino-terminal 20 amino acids were followed by 18 hydrophobic amino acids which presumably function as a transmembrane anchor. This lack of a signal sequence, the presence of an internal hydrophobic domain, and the presence of two potential N-linked glycosylation sites in the C-terminal domain (at amino acids $Asn^{63}$ and $Asn^{170}$) suggested that CD27L is a type II transmembrane protein, which has an extracellular carboxy-terminal domain.

The isolated cDNA clone contained only 37 nucleotides upstream of the presumed initiation codon (SEQ ID NO: 1) with no in-frame termination codons. In addition, the sequence around this initiation site does not conform to the consensus for such sites as predicted by Kozak, *Nucl. Acids. Res.* 12:857 (1984). Thus, an "anchored PCR" reaction was carried out according to Carrier et al., *Gene* 116:173 (1992) to clone the 5' end of the CD27L transcript to ensure that there was not an upstream initiation site. This resulted in the identification of an additional 113 nucleotides preceding the end of the isolated clone (SEQ ID NO: 1). No initiation sites were found upstream of that which was previously identified.

EXAMPLE 5

Monoclonal Antibodies to CD27L

This example illustrates the preparation of monoclonal antibodies to CD27L. CD27L is expressed in mammalian host cells such as COS-7 or CV-1/EBNA-1 cells and purified using CD27/Fc affinity chromatography. Purified CD27L can be used to generate monoclonal antibodies against CD27L using conventional techniques, for example, those techniques described in U.S. Pat. No. 4,411,993. Briefly, mice are immunized with CD27L as an immunogen emulsified in complete Freund's adjuvant, and injected in amounts ranging from 10–100 μg subcutaneously or intraperitoneally. Ten to twelve days later, the immunized animals are boosted with additional CD27L emulsified in incomplete Freund's adjuvant. Mice are periodically boosted thereafter on a weekly to bi-weekly immunization schedule. Serum samples are periodically taken by retroorbital bleeding or tail-tip excision for testing by dot blot assay or ELISA (Enzyme-Linked Immunosorbent Assay), for CD27L antibodies.

Following detection of an appropriate antibody titer, positive animals are provided one last intravenous injection of CD27L in saline. Three to four days later, the animals are sacrificed, spleen cells harvested, and spleen cells are fused to a murine myeloma cell line (e.g., NS1 or Ag 8.653). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified CD27L by adaptations of the techniques disclosed in Engvall et al., *Immunochem.* 8:871, 1971 and in U.S. Pat. No. 4,703,004. Positive hybridoma cells can be injected intraperitoneally into syngeneic BALB/c mice to produce ascites containing high concentrations of anti-CD27L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to CD27L.

EXAMPLE 6

Binding of CD27L to CD27

To compare the binding of CD27 to the native CD27L expressed on MP-1 cells with that of the cloned CD27L expressed on transfected CV-1/EBNA cells, a modified indirect binding assay was devised using the CD27/Fc and the $^{125}$I-labeled mouse anti-human IgG antibodies described in Example 2. This was necessary because direct radiolabeling of CD27/Fc resulted in its inactivation. MP-1 cells were exposed to varying concentrations of CD27/Fc, followed by a constant saturating concentration of $^{125}$I-antibody against the Fc portion of the molecule as follows.

Binding assays for MP-1 cells were conducted by growing cells in suspension culture in 96-well culture plates. Briefly, MP-1 cells ($2\times10^6$ cells/well) were incubated in the presence or absence of various concentrations of CD27/Fc in binding medium (RPMI 1640 medium, 1% bovine serum albumin, 0.2% sodium azide and 20 mM Hepes, pH 7.2) for one hour at 37° C. Cells were then washed once with PBS and incubated with $^{125}$I-mouse anti-human IgG (40 ng/ml) in binding medium with gentle agitation for one hour at 37° C. Cells and unbound $^{125}$I-antibody were separated by the pthalate oil separation method, essentially as described by Dower et al., *J. Immunol.* 132:751 (1984).

Monolayers of CV-1/EBNA cells ($2.5\times10^5$ cells per well) transfected with the MP-1 cDNA pools were assayed for CD27L expression after two days using mouse anti-human IgG binding and slide autoradiography. Transfected cell monolayers were washed with binding medium containing non-fat dry milk (50 mg/ml; BM-NFDM), then incubated with CD27/Fc in BM-NFDM (1 μg/ml) for one hour at room temperature. Cells were then washed three times with BM-NFDM and incubated with 40 ng/ml $^{125}$I-mouse anti-human IgG in BM-NFDM for one hour. Cells were washed twice with BM-NFDM, three times with PBS, and fixed in PBS containing 2.5% gluteraldehyde for 30 minutes, washed twice more with PBS and air dried. The chamber slides were then dipped in Kodak GTNB-2 photographic emulsion and exposed for 3 days at room temperature before developing.

For binding assays on the cloned CD27L, adherent CV-1/EBNA cells were transfected with the CD27L expression plasmid in 12-well plates ($2.5\times10^5$ cells/well) as above. Two days later cells were washed with BM-NFDM and incubated with various concentrations of CD27/Fc. Subsequently, cells were washed, incubated with $^{125}$I-labeled mouse anti-human IgG antibody as described previously, and harvested by trypsinization. In all assays, non-specific binding of $^{125}$I antibody was assayed in the absence of CD27/Fc as well as in the presence of CD27/Fc and 200-fold molar excess of unlabeled antibody. Free and cell-bound $^{125}$I-antibody were quantified on a Packard Autogamma Counter. Affinity calculations were generated on RS/1 (BBN Software, Boston, Mass.) run on a Microvax computer.

When the MP-1 binding data was replotted in the Scatchard coordinate system, a biphasic curve was generated indicating both high- and low-affinity binding components. The CD27L expressed on MP-1 cells had Ka values of $1.58\times10^9 M^{-1}$ and $1.83\times10^8 M^{-1}$, with 250 and 560 sites per cell, respectively. Similarly, the cloned CD27L expressed in CV-1/EBNA cells demonstrated both high- and low-affinity binding components. The affinity constants generated from Scatchard analysis, $2.7\times10^9 M^{-1}$ and $1.2\times10^8 M^{-1}$, match well with those observed for binding of CD27/Fc to the native ligand expressed on MP-1 cells. Overall, the expression of the ligand was enhanced on CV-1/EBNA cells with 12,017 high-affinity and 68,560 low affinity binding sites per cell detected.

EXAMPLE 7

SDS-Polyacrylamide Gel Electorphoresis of CD27L

Native and recombinant CD27L protein was analyzed by SDS-PAGE under reducing conditions as follows. Cells were surface-labeled with $^{125}$I as previously described by Urdal et al., (*J. Biol. Chem.* 263:2870 (1988). Membrane proteins were solubilized with detergent in the presence of protease inhibitors including 100 mM iodoacetamide. CD27L was isolated by binding to CD27/Fc and protein G sepharose (Armitage et al., *Nature* 357:80, (1992). To eliminate binding of CD27/Fc to Fc receptors, detergent lysates were precleared with 50 μg/ml human IgG and 5% rabbit and goat sera. Samples were resuspended in buffer containing 4M urea and 5% 2-mercaptoethanol, and electrophoresed through 4–20% gradient SDS-polyacrylamide gels (NOVEX).

Figure 6:
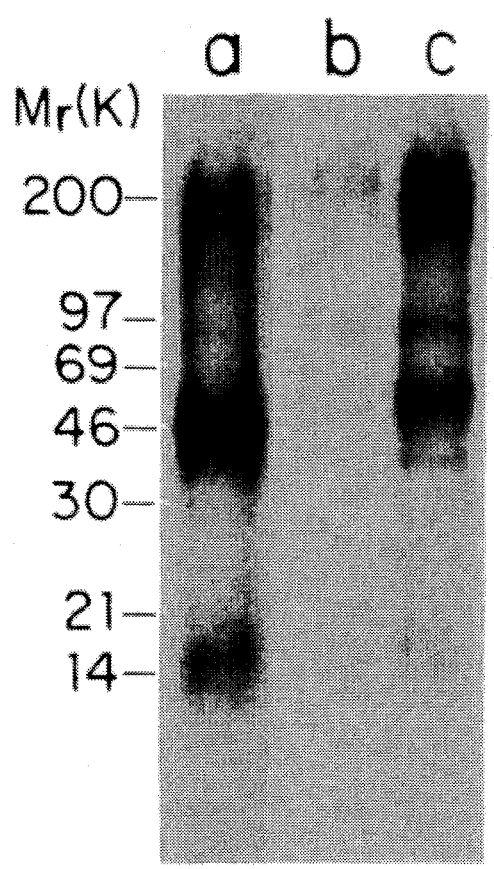
FIG. 6 is an SDS-polyacrylamide gel electrophoresis of CD27L (as described in detail in Example 7). MP-1 cells (lane a) and CV-1/EBNA cells transfected with empty vector (land b) or vector expressing CD27L (lane c) were surface labeled with $^{125}$I-sodium. Lysates were then precipitated with CD27/Fc followed by protein G-Sepharose and analyzed on SDS-polyacrylamide (4%–20%) gels under reducing conditions. The gel shows that the predominant protein species on both MP-1 and CD27L-expressing CV-1/EBNA cells had an apparent $M_r$ of about 50,000.

As shown in FIG. 6, the predominant protein species observed on both MP-1 and CD27L-expressing CV-1/EBNA cells had an apparent $M_r$ of ~50,000. Comparison with the calculated $M_r$ (21,146) of the unmodified CD27L suggests that the N-linked glycosylation sites in the extracellular domain are used. Precipitates from both cells also demonstrated a minor protein species of approximately 20,000 which was not found in control CV-1/EBNA cells (FIG. 6). This could be either unmodified CD27L or the product of protein degradation. A protein species of ~200 kDa was also observed which is specifically precipitated using CD27/Fc.

EXAMPLE 8

Biological Activity of CD27L

A. CD27L Stimulates T Cell Proliferation

The ability of CD27L to stimulate proliferation of human peripheral blood T cells was shown using the following proliferation assay. Human peripheral blood T cells were purified from PBMC by rosetting with 2-aminoethyl-isothiouronium bromide hydrobromide-treated SRBC. After hypotonic lysis of SRBC, monocytes were depleted by plastic adherence for 1 hr at 37° C. $CD^{4+}$ and $CD^{8+}$ T cells were purified by negative depletion of $CD^{8+}$ or $CD^{4+}$ cells, respectively, using magnetic cell sorting according to the manufacturer's protocol (Miltenyi Biotec, Sunnyvale, Calif.). Sorted cells were routinely >95% pure, as assessed by flow cytometry. T cells were cultured in 96-well plates at $10^5$ cells per well in triplicate for 3 days in the presence of a sub-optimal concentration of phytohemagglutanin (0.1. % v/v). Also present in the cultures were CV-1/EBNA cells that were fixed at 2 days post-transfection with 1% paraformaldehyde for 5 min at 25° C. Wells were pulsed with 1 μCi of tritiated thymidine for the final 8 hr of culture and c.p.m. incorporation determined. A neutralizing IL-2 antiserum, prepared in a rabbit, was used to block IL-2 bioactivity at a dilution of 1:500, as previously described by Alderson et al., *J. Exp. Med.* 172: 577 (1990).

As shown in FIG. 1, the addition of CV-1/EBNA cells expressing CD27L to T cells in the presence of a sub-optimal concentration of phytohemagglutinin (PHA) resulted in enhanced thymidine incorporation, whereas addition of control CV-1/EBNA cells transfected with empty vector had no effect. As few as 100 CV-1/EBNA cells expressing CD27L were sufficient to significantly enhance proliferation in cultures established with $1 \times 10^5$ T cells. In contrast, in the absence of co-stimulation CD27L had no effect on T-cell proliferation.

Figure 2:
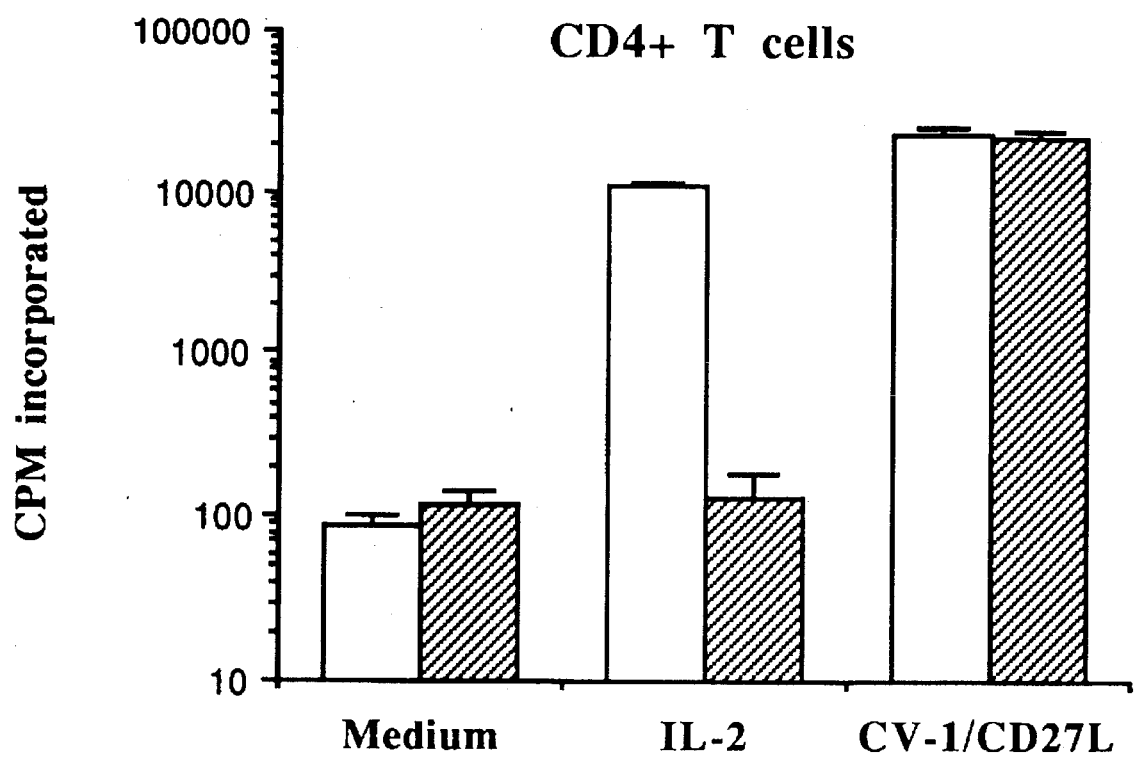
Figure 3:
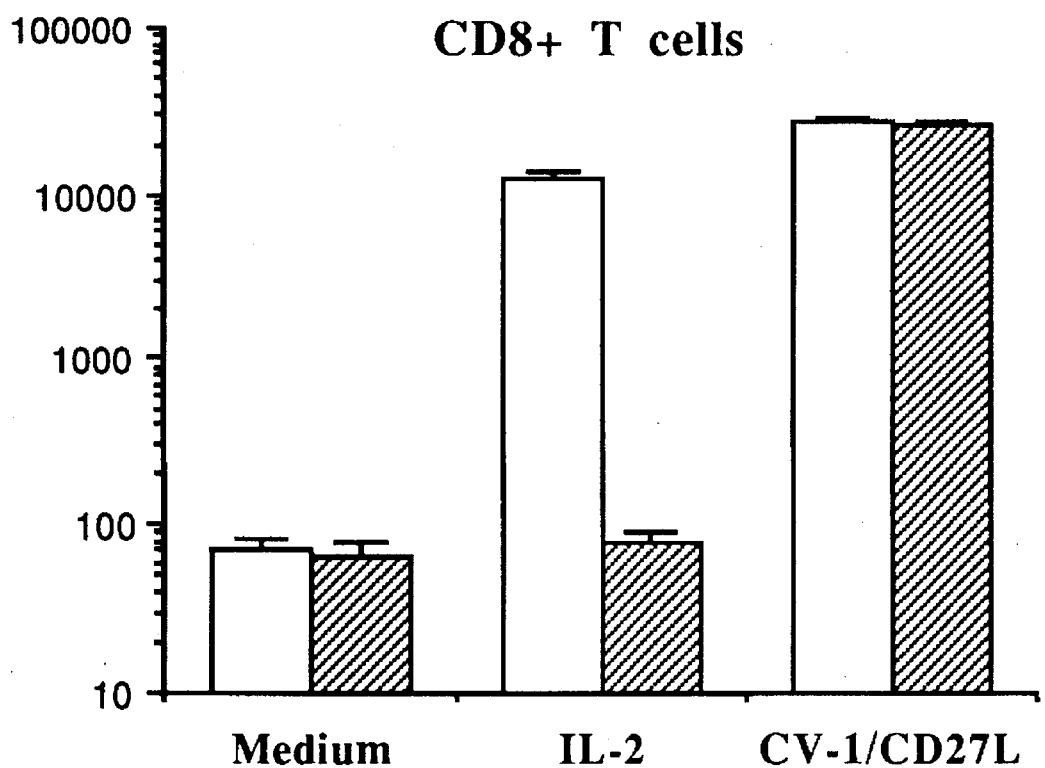

By using magnetic beads to isolate sub-populations of T cells, it was determined that CD27L co-stimulated the proliferation of both $CD^{4+}$ and $CD^{8+}$ T cells (FIGS. 2 and 3). In addition, the induction of $CD^{4+}$ and $CD^{8+}$ T-cell proliferation by CD27L was unaffected by the presence of an IL-2-neutralizing antiserum, implying that under these culture conditions CD27L-mediated T-cell proliferation is independent of IL-2. Thus, CD27L either delivers a direct proliferative signal to at least some T cells or, alternatively, that cytokines other than IL-2 may contribute to the response.

B. CD27 Induces Lytic Activity of T Cells

To further characterize the effect of CD27L on T cells, its ability to affect the in vitro generation of cytolytic cells in the presence or absence of lectin was assessed. Culture conditions for measuring cytolytic activity were as described above for proliferation assays except that T cells were cultured for 4 days in 24-well plates at $10^6$ cells per well using a fixed concentration ($10^5$) of CV-1/EBNA cells. A 4 hr $^{51}$Cr-release assay was used to assess cytolytic activity of cultured cells as previously described (Alderson et al., *J. Exp. Med.* 172:577 (1990). Briefly, cultured cells were washed in culture medium and duplicate culture fractions serially diluted in 96-well v-bottomed plates. As a target cell, the murine tumor cell line P815 was used in the presence of PHA (0.6% v/v) in order to reveal lytic cells regardless of their specificity. One lytic unit (LU) was defined as the fraction of the initial culture giving rise to 50% lysis of the target cells.

Figure 4:
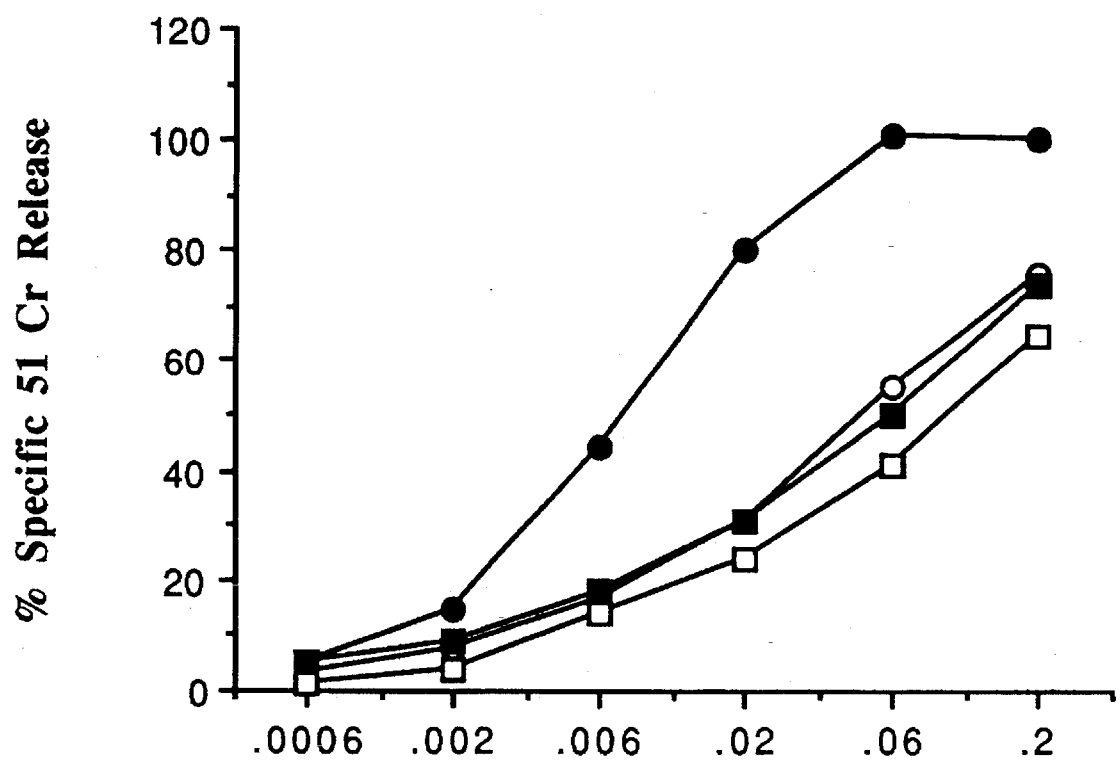
FIGS. 4 and 5 show that CD27L induces cytolytic T cells (as described in detail in Example 8B ). Purified T cells were cultured in medium alone (o), in medium plus IL-2 (●), or with CV-1/EBNA cells transfected with empty vector (□) or with vector expressing CD27L (■) either in the absence (FIG. 4) or in the presence (FIG. 5) of a sub-optimal concentration of PHA (0.1%). After 4 days, cells were recovered and assessed in duplicate for cytolytic activity against $^{51}$Cr-labeled P815 targets in the presence of PHA (0.6%).
Figure 5:
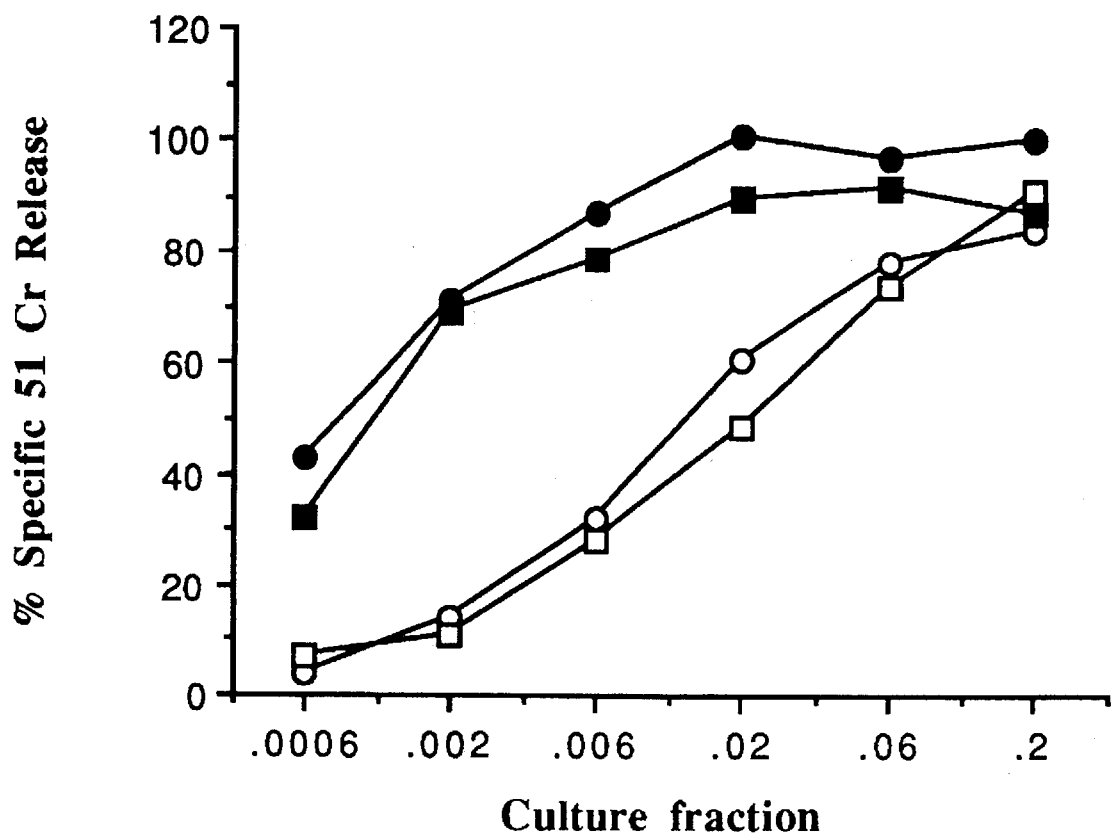

CD27L had no stimulatory effect on cytolytic activity in the absence of co-stimulation, as detected in a lectin-mediated cytotoxicity assay (FIG. 4). However, incubation of purified T cells with CD27L in the presence of sub-optimal PHA resulted in the enhanced generation of cytolytic cells compared to cells cultured with PHA alone or PHA plus control CV-1/EBNA cells (FIG. 5). The lytic activity induced by CD27L on PHA co-stimulated T cells in this assay was comparable to that induced by IL-2 (1,100 and 800 lytic units (LU) per culture, respectively) and was more than ten-fold greater than that seen with cells incubated in the presence of PHA alone (61 LU) or PHA plus control CV-1/EBNA cells (50 LU). The effect of CD27L on cytolytic cell generation was also apparent on a per effector cell basis (780 LU per $10^6$ cells for CD27L+PHA compared to 71 LU per $10^6$ cells for control CV-1/EBNA cells+PHA) implying that in addition to supporting T cell proliferation, CD27L enhances the differentiation of cytolytic T cell precursors.

EXAMPLE 9

Construction and Expression of Soluble CD27L

A CD27-L DNA was constructed to express a soluble, oligomeric CD27-L fusion protein referred to as sCD27L-3. The construct encoding sCD27L-3 (shown in SEQ ID NO: 9 and SEQ ID NO: 10) contains a leader sequence (comprising amino acids −24 through −1), a 37 amino acid sequence comprising a leucine zipper domain (comprising amino acids 3–35), and the extracellular region of human CD27-L (comprising amino acids 39–193). The nucleotides encoding amino acids 1–2 and 36–38 are non-functional residuals of restriction sites. The construct was prepared by using methods that are well-known in the art to obtain a DNA encoding the extracellular region of CD27-L. Briefly, the extracellular region of CD27-L was amplified from a full-length CD27-L cDNA using PCR. The primers used were derived from the extracellular region of CD27-L (SEQ ID NO: 1, nucleotides 222–245, for the 5' primer, and the complement of nucleotides 663–689 for the 3' primer) with addition of sequences encoding desired restriction enzyme sites (ACTAGT, which contains a Spe I site, for the 5' primer, and GCGGCCGC, which contains a Not I site, for the 3' primer). The amplified PCR product, representing the extracellular domain of CD27-L, was cloned into an Spe I/Not I-cut SMAG (pDC206) vector. SMAG vector is a derivative of pDC201 (Sims et al., *Science* 241:585, 1988) that contains the murine IL-7 leader sequence. The vector was amplified, then cut with Spe I and treated with calf intestinal alkaline phosphatase. The sequence of nucleotides comprising the leucine zipper region were synthesized by ligating multiple oligonucleotides derived from the known amino acid sequence of the leucine zipper using standard methodology, and then ligating with the Spe I-cut SMAG vector, to form an expression vector comprising a murine IL-7 leader sequence (Namen et al., *Nature* 333:571; 1988), a leucine zipper domain, and the extracellular domain of CD27-L. The expression vector was referred to as pDC206/sCD27L-3.

pDC206/sCD27L-3 was co-transfected into the monkey kidney cell line CV-1/EBNA (ATCC CRL 10478) along with a pSV3Neo plasmid. pSV3Neo (Mulligan and Berg, *Proc. Natl. Acad. Sci. U.S.A.* 78:2072; 1981) is a plasmid which expresses the SV40 T antigen, and thus allows for the episomal replication of the pDC206 plasmid.

Once cells expressing the fusion construct are identified, large scale cultures of transfected cells are grown to accumulate supernatant from cells expressing the soluble, oligomeric CD27-L fusion protein (referred to as sCD27L-3). sCD27L-3 in supernatant fluid is purified by affinity purification substantially as described in U.S. Pat. No. 5,011,912. sCD27L-3 may also be purified using other protein purification methods, as described herein. Silver-stained SDS gels of the soluble, oligomeric CD27-L fusion protein can be prepared to determine purity. sCD27L-3 binds to soluble CD27, and inhibits binding of soluble CD27 to cells expressing CD27-L, as described in Example 10.

EXAMPLE 10

Biological Activity of Soluble CD27L

This example illustrates a biological activity of sCD27L-3. A soluble form of the human lymphocyte surface antigen CD27 was prepared substantially as described by Fanslow et al., *J. Immunol.* 149:65 (1992), to form a dimeric, Fc fusion construct referred to as CD27/Fc. CD27/Fc comprises the extracellular region of CD27 and an Fc region from a human IgG$_1$. sCD27L-3 inhibits binding of CD27/Fc to MP-1 cell, a human, Epstein-Barr virus-transformed B cell line that expresses endogenous CD27-L.

Conditioned supernatant fluid from CV-1/EBNA cells transfected with pDC206/sCD27L-3 was titrated in a 96 well plate. A constant amount of CD27/Fc (1 μg/well) was added to each well, followed by 1–2×10$^6$ MP-1 cells per well, in binding medium (RPMI-1640 containing 1% bovine serum albumin, 0.2 % sodium azide and 20 mM HEPES, pH 7.2). The plate was incubated at 37° C. for one hour. Cells were washed twice with PBS, then pelleted by centrifugation. $^{125}$I-mouse anti-human IgG Fc was added to each well at a constant concentration, and the plate incubated for an additional hour at 37° C. The $^{125}$I-mouse anti-human IgG Fc bound to the CD27/Fc that bound to the MP-1 cells. After the final incubation, cells were harvested over phthalate oil-containing tubes to separate the bound and free $^{125}$I-mouse anti-human IgG Fc, and the amount of radioactivity quantitated using a gamma counter.

sCD27L-3 exhibited a dose-dependent inhibition of the binding of CD27/Fc to MP-1 cells. By comparing the concentration at which the inhibition of binding of CD27/Fc is at 50% to the titration of inhibition by sCD27L-3, it was estimated that the concentration of sCD27L-3 in the conditioned medium was between 18 and 40 μg/ml. In making this comparison, the MW of sCD27L-3 was estimated to be 135 Kd (estimated MW of extracellular region of CD27-L was 45 Kd, multiplied by three for formation of trimer), and the binding of sCD27L-3 to CD27/Fc was assumed to occur at a molar ratio. The $K_i$ was estimated to be 10 times the $K_a$, which was $3 \times 10^{-7} M^{-1}$, and the initial concentration was assumed to be $1 \times 10^{-8} M$. The results demonstrated that the initial assumption of a concentration of $1 \times 10^{-8} M$ was approximately 10-fold too low, and a 1:3 dilution of the supernatant fluid actually gave an estimated concentration of $1 \times 10^{-7} M$.

---

What is claimed is:

1. An isolated DNA sequence encoding a non-antibody CD27L polypeptide stimulates T cell proliferation and T cell lytic activity, wherein the DNA sequence is selected from the group consisting of:
   (a) cDNA obtained from the coding region of the sequence shown in Sequence I.D. No. 1; and
   (b) DNA sequences that are degenerate as a result of the genetic code to a DNA sequence of (a).

2. An isolated DNA sequence according to claim 1, wherein the CD27L polypeptide is a soluble CD27L polypeptide.

3. An expression vector comprising a DNA sequence according to claim 2.

4. A host cell transformed or transfected with an expression vector according to claim 3.

5. A process for preparing a CD27L polypeptide, comprising culturing a host cell according to claim 4 under conditions promoting expression of CD27L and recovering the CD27L polypeptide from the culture.

6. An expression vector comprising a DNA sequence according to claim 1.

7. A host cell transformed or transfected with an expression vector according to claim 6.

8. A process for preparing a CD27L polypeptide, comprising culturing a host cell according to claim 7 under conditions promoting expression of CD27L, and recovering the CD27L polypeptide from the culture.

9. The isolated DNA sequence according to claim 1 wherein the cDNA encodes a soluble CD27L consisting of amine acids number 39 to 193 of Sequence ID No. 1.

10. A purified CD27L polypeptide which stimulates T cell proliferation and T cell lytic activity, said polypeptide having an amino acid sequence shown in Sequence I.D. No. 2.

11. The purified CD27L polypeptide according to claim 10 wherein said polypeptide is a soluble CD27L polypeptide.

12. An oligomeric CD27L polypeptide comprising two or more polypeptides of claim 10 fused to one another.

* * * * *

UNITED STATES PATENT AND TRADEMARK OFFICE
CERTIFICATE OF CORRECTION

PATENT NO.    : 5,573,924
DATED         : November 12, 1996
INVENTOR(S)   : M. Patricia Beckmann et al.

It is certified that error appears in the above identified patent and that said Letters Patent is hereby corrected as shown below:

In column 39, claim 1, line 9, following "polypeptide" please insert --which--.

In column 40, claim 9, line 17, please delete "amine" and insert therefor --amino--.

Signed and Sealed this

Third Day of June, 1997

Attest:

BRUCE LEHMAN

*Attesting Officer*

*Commissioner of Patents and Trademarks*